United States Patent
Hershberg

(10) Patent No.: US 10,016,440 B2
(45) Date of Patent: Jul. 10, 2018

(54) METHODS OF ENHANCING ANTIBODY-DEPENDENT CELLULAR CYTOTOXICITY

(75) Inventor: Robert Hershberg, Seattle, WA (US)

(73) Assignee: VentiRx Pharmaceuticals, Inc., Seattle, WA (US)

( * ) Notice: Subject to any disclaimer, the term of this patent is extended or adjusted under 35 U.S.C. 154(b) by 336 days.

(21) Appl. No.: 13/092,088

(22) Filed: Apr. 21, 2011

(65) Prior Publication Data

US 2012/0003213 A1    Jan. 5, 2012

Related U.S. Application Data

(60) Provisional application No. 61/326,406, filed on Apr. 21, 2010.

(51) Int. Cl.
| | |
|---|---|
| A61P 29/00 | (2006.01) |
| A61K 31/55 | (2006.01) |
| A61K 39/395 | (2006.01) |
| A61K 45/06 | (2006.01) |
| C07K 16/28 | (2006.01) |
| C07K 16/32 | (2006.01) |
| A61K 39/39 | (2006.01) |

(Continued)

(52) U.S. Cl.
CPC .......... *A61K 31/55* (2013.01); *A61K 39/39* (2013.01); *A61K 39/395* (2013.01); *A61K 39/39558* (2013.01); *A61K 45/06* (2013.01); *C07K 16/2863* (2013.01); *C07K 16/2887* (2013.01); *C07K 16/3046* (2013.01); *C07K 16/32* (2013.01); *A61K 2039/505* (2013.01); *A61K 2300/00* (2013.01); *C07K 2317/21* (2013.01); *C07K 2317/24* (2013.01); *C07K 2317/732* (2013.01)

(58) Field of Classification Search
CPC .. A61K 2300/00; A61K 31/55; A61K 39/395; A61K 39/39558
See application file for complete search history.

(56) References Cited

U.S. PATENT DOCUMENTS

| | | | |
|---|---|---|---|
| 5,373,737 | A | 12/1994 | Hwang |
| 5,602,345 | A | 2/1997 | Wenger et al. |
| 5,936,156 | A | 8/1999 | Roberts et al. |

(Continued)

FOREIGN PATENT DOCUMENTS

| | | |
|---|---|---|
| RU | 2366664 C2 | 1/2006 |
| RU | 2379056 C2 | 3/2006 |

(Continued)

OTHER PUBLICATIONS

Butchar et al. Reciprocal regulation of activating and inhibitory Fcgamma receptors by TLR7/8 activation: implications for tumor immunotherapy. Clin. Cancer Res. 2010; 16: 2065-2075.*

(Continued)

*Primary Examiner* — Anna Pagonakis
(74) *Attorney, Agent, or Firm* — Cooley LLP; Heidi A. Erlacher; Chun L. Yu

(57) ABSTRACT

The application relates to method of increasing antibody-dependent cellular cytotoxicity in a subject receiving therapeutic monoclonal antibody treatment. In some embodiments, methods are provided for administering to subject to a subject in need thereof a therapeutic antibody in conjunction with an ADCC enhancer molecule.

8 Claims, 5 Drawing Sheets

(51) Int. Cl.
C07K 16/30 (2006.01)
A61K 39/00 (2006.01)

(56) References Cited

U.S. PATENT DOCUMENTS

| | | | |
|---|---|---|---|
| 6,043,238 | A | 3/2000 | Cooper et al. |
| 2002/0102255 | A1 | 8/2002 | Chang |
| 2003/0072762 | A1 | 4/2003 | van de Winkel et al. |
| 2003/0139364 | A1 | 7/2003 | Krieg et al. |
| 2005/0037002 | A1 | 2/2005 | Velardi et al. |
| 2005/0066710 | A1 | 3/2005 | Lin |
| 2005/0191342 | A1 | 9/2005 | Tam et al. |
| 2006/0241076 | A1 | 10/2006 | Uhlmann et al. |
| 2008/0234251 | A1 | 9/2008 | Doherty et al. |
| 2009/0131453 | A1 | 5/2009 | Seal et al. |
| 2010/0029585 | A1 | 2/2010 | Howbert et al. |
| 2010/0216989 | A1 | 8/2010 | Howbert et al. |
| 2013/0236449 | A1 | 9/2013 | Hershberg |
| 2017/0027954 | A1 | 2/2017 | Hershberg |

FOREIGN PATENT DOCUMENTS

| | | |
|---|---|---|
| WO | WO-07024612 A2 | 3/2007 |
| WO | WO-09131453 A1 | 10/2009 |
| WO | WO-09149306 A2 | 12/2009 |
| WO | WO-10054215 A1 | 5/2010 |

OTHER PUBLICATIONS

Zhang et al. "FCGR2A and FCGR3A Polymorphisms Associated with Clinical Outcome of Epidermal Growth Factor Receptor-Expressing Metastatic Colorectal Cancer Patients Treated With Single-Agent Cetuximab." *J. Clin. Oncol.* 25.24(2007):3712-3718.
Andrade Filho et al. "Novel Immunogenic HLA-A*0201-Restricted Epidermal Growth Factor-Specific T-Cell Epitope in Head and Neck Cancer Patients." *J. Immunother.* 33.1(2010):83-91.
Bergmann et al. "T Regulatory Type 1 Cells in Squamous Cell Carcinoma of the Head and Neck: Mechanisms of Suppression and Expansion in Advanced Disease." *Clin. Cancer Res.* 14.12(2008):3706-3715.
Bonner et al. "Radiotherapy Plus Cetuximab for Locoregionally Advanced Head and Neck Cancer: 5-Year Survival Data From a Phase 3 Randomised Trial, and Relation Between Cetuximab-Induced Rash and Survival." *Lancet Oncol.* 11.1(2010):21-28.
Diebold. "Recognition of Viral Single-Stranded RNA by Toll-Like Receptors." *Adv. Drug Deliv. Rev.* 60.7(2008):813-823.
Dudek et al. "First in Human Phase I Trial of 825A, a Novel Systemic Toll-Like Receptor 7 Agonist, to Activate Innate Immune Responses in Patients With Advanced Cancer." *Clin. Cancer Res.* 13.23(2007):7119-7125.
Dummer et al. "An Exploratory Study of Systemic Administration of the Toll-Like Receptor-7 Agonist 852A in Patients With Refractory Metastatic Melanoma." *Clin. Cancer Res.* 14.3(2008):856-864.
Hamm et al. "Cancer Immunotherapeutic Potential of Novel Small Molecule TLR7 and TLR8 Agonists." *J. Immunotoxicol.* 6.4(2009):257-265.
Hart et al. "TLR7/8-Mediated Activation of Human NK Cells Results in Accessory Cell-Dependent IFN-γ Production." *J. Immunol.* 175.3(2005):1636-1642.
Heil et al. "Species-Specific Recognition of Single-Stranded RNA via Toll-Like Receptor 7 and 8." *Science.* 303.5663(2004):1526-1529.
Hiroishi et al. "Strong CD8(+) T-Cell Responses Against Tumor-Associated Antigens Prolong the Recurrence-Free Interval After Tumor Treatment in Patients With Hepatocellular Carcinoma." *J. Gastroenterol.* 45.4(2010):451-458.
Hornung et al. "Quantitative Expression of Toll-Like Receptor 1-10 mRNA in Cellular Subsets of Human Peripheral Blood Mononuclear Cells and Sensitivity to CpG Oligodeoxynucleotides." *J. Immunol.* 168.9(2002):4531-4537.
Kawai et al. "TLR Signaling." *Semin. Immunol.* 19.1(2007):24-32.
Lebwohl et al. "Imiquimod 5% Cream for the Treatment of Actinic Keratosis: Results From Two Phase III, Randomized, Double-Blind, Parallel Group, Vehicle-Controlled Trials." *J. Am. Acad. Dermatol.* 50.5(2004):714-721.
Lombardi et al. "Human Dendritic Cells Stimulated via TLR7 and/or TLR8 Induce the Sequential Production of II-10, IFN-γ, and IL-17A by Naive CD4+ T Cells." *J. Immunol.* 182.6(2009):3372-3379.
Lopez-Albaitero et al. "Immune Activation by Epidermal Growth Factor Receptor Specific Monoclonal Antibody Therapy for Head and Neck Cancer." *Arch. Otolaryngol. Head Neck Surg.* 133.12(2007):1277-1281.
Lopez-Albaitero et al. "Role of Polymorphic Fc γ Receptor IIIa and EGFR Expression Level in Cetuximab Mediated, NK Cell Dependent in vitro Cytotoxicity of Head and Neck Squamous Cell Carcinoma Cells." *Cancer Immunol. Immunother.* 58.11(2009):1853-1864.
McDonnell et al. "Tumor Antigen Cross-Presentation and the Dendritic Cell: Where it All Begins?" *Clin. Dev. Immunol.* 2010(2010). ID# 539519.
Okamura et al. "Cloning of a New Cytokine That Induces IFN-γ Production by T Cells." *Nature.* 378.6553(1995):88-91.
Oldfield et al. "Imiquimod: In Superficial Basal Cell Carcinoma." *Am. J. Clin. Dermatol.* 6.3(2005):195-200.
Peng et al. "Toll-Like Receptor 8-Mediated Reversal of CD4+ Regulatory T Cell Function." *Science.* 309.5739(2005):1380-1384.
Sauder et al. "Randomized, Single-Blind, Placebo-Controlled Study of Topical Application of the Immune Response Modulator Resiquimod in Healthy Adults." *Antimicrob. Agents Chemother.* 47.12(2003):3846-3852.
Schön et al. "TLR7 and TLR8 as Targets in Cancer Therapy." *Oncogene.* 27.2(2008):190-199.
Smits et al. "The Use of TLR7 and TLR8 Ligands for the Enhancement of Cancer Immunotherapy." *Oncologist* 13.8(2008):859-875.
Strauss et al. "The Frequncy and Suppressor Function of CD4+CD25highFoxp3+ T Cells in the Circulation of Patients With Squamous Cell Carcinoma of the Head and Neck." *Clin. Cancer Res.* 13.21(2007):6301-6311.
Whiteside et al. "Immune Cells in the Tumor Microenvironment." *Gene Therapy of Cancer.* Walden et al., eds. New York: Plenum Press. 451(1998):167-171.
Xu et al. "Regulation of Antitumor Immune Responses by the IL-12 Family Cytokines, IL-12, IL-23, and IL-27." *Clin. Dev. Immunol.* 2010(2010). ID# 832454.
Lu et al. "VTX-2337 is a Novel TLR8 Agonist That Activates NK Cells and Augments ADCC." *Clin. Cancer Res.* 18(2012):499-509.
ACUC (Surface Area to Weight Ratio Conversion Factor, 2007, https ://ncifrederick.cancer.gov /lasp/acuc/frederick/Media/Documents/ ACUC42.pdf).
Belikov V.G., Pharmaceutical Chemistry, M., Higher Education, 1993, p. 43-47.
Bibeau et al. " Impact of FcγRIIa-FcγRIIIa Polymorphisms and *KRAS*Mutations on the Clinical Outcome of Patients With Metastatic Colorectal Cancer Treated With Cetuximab Plus Irinotecan", J. Clin. One. 2009, vol. 27, No. 7, p. 1122-1129.
Friedberg et al. "Phase II study of a TLR-9 agonist (1018 ISS) with rituximab in patients with relapsed or refractory follicular lymphoma", Brit. J. of Haematology, 2009, vol. 146, p. 282-291.
Kholodov L.E. et al., "Clinical Pharmacokinetics", M., "Medicine", 1985, p. 82-85, 90-97, 134-139, 378-380.
"Molecular pharmacology: a short course", ed. P.V. Sergeev, M., 1975, p. 10.
Moreno et al. "Toll-like receptor agonists and invariant natural killer T-cells enhance antibody-dependent cell-mediated cytotoxicity (ADCC)", Cancer Letters 2008, vol. 272, p. 70-76.
Ogino, S. et al. "Sensitive Sequencing Method for KRAS Mutation Detection by Pyrosequencing" Journal of Molecular Diagnostics, 2005, vol. 7, No. 3, p. 413-421.
Okamura et al. "Cloning of a New Cytokine That Induces IFN-γ Production by T Cells."Nature, 1995, vol. 378, p. 88-91.

(56) References Cited

OTHER PUBLICATIONS

Rubio, I. et al. "Farnesylation of Ras is important for the interaction with phosphoinositide 3-kinase γ" Eur. J. Biochem., 1999, vol. 266, p. 70-82.

Saridaki, Z. et al. "Mechanisms of resistance to anti-EGFR monoclonal antibody treatment in metastatic colorectal cancer", World Journal of Gastroenterology, 2010, vol. 16, No. 10, p. 1177-1187.

Vos, M. et al. "RASSF2 Is a Novel K-Ras-specific Effector and Potential tumor Suppressor" Journal of Biological Chemistry, 2003, vol. 278, No. 30, p. 28045-28051.

Wu L. et al. "Lenalidomide enchances natural killer cell and monocyte mediated antibody-dependent cellular cytotoxicity of rituximab-treated CD20$^+$tumor cells", Clinical Cancer Research, 2008, vol. 14, No. 14, p. 4650-4657.

\* cited by examiner

METHODS OF ENHANCING ANTIBODY-DEPENDENT CELLULAR CYTOTOXICITY

CROSS-REFERENCE TO RELATED APPLICATION

This application claims the benefit of U.S. Ser. No. 61/326,406, filed Apr. 21, 2010, the contents of which are incorporated herein by reference in its entirety.

FIELD OF THE DISCLOSURE

Embodiments of the present disclosure are directed to methods of enhancing the cytotoxicity of therapeutic monoclonal antibodies for the treatment of cancer and other cellular diseases.

BACKGROUND OF THE DISCLOSURE

Monoclonal antibodies (MAbs) have demonstrated clinical effectiveness in a variety of malignancies. Monoclonal antibodies are now being commonly used as therapeutic agents for the treatment and/or prevention of cancers, autoimmune diseases, thrombosis, inflammation, and infection. However, there are some instances of low antibody activity contributing to insufficient therapeutic effects on cancers, autoimmune diseases, inflammation, and infection. Such insufficient drug action may lead to increased dosages and cost required for treatment. Under these circumstances, enhancement of the therapeutic activity of the monoclonal antibodies is an important objective.

Therapeutic monoclonal antibodies are preferably capable of antibody-dependent cellular cytotoxicity (ADCC), particularly when used in the treatment of cancers or other cellular diseases. That is, therapeutic MAbs preferably exert cytotoxic effects against their target cells, such as target cancer cells or lymphocytes. Such antibodies bind to antigens on the surface of target cells, via their Fc domain, to Fc receptors on the surface of effector cells such as NK cells and macrophages, thereby exerting damage on target cells. This mechanism is antibody-dependent cellular cytotoxicity (ADCC). Alternatively, antibodies damage cells by activating complement via the Fc domain. This is called complement-dependent cytotoxicity (CDC). Such antibody activities exerted via Fc domains are called effector activities.

There have been various attempts to enhance the effector function of antibodies with the aim of enhancing their therapeutic activity. Several types of effector cells, such as monocytes, neutrophils, and natural killer (NK) cells, have surface receptors that bind the Fc portion of immunoglobulins. Effector cells for inducing ADCC against a target cell include human leukocytes, macrophages, monocytes, activated neutrophils, and possibly activated natural killer (NK) cells and eosinophils. Preferred effector cells express FcγRI and include, for example, monocytes and activated neutrophils. Expression of FcγRI has been found to be up-regulated by interferon gamma (IFN-γ). This enhanced expression increases the cytotoxic activity of monocytes and neutrophils against target cells.

An Fc receptor is a protein found on the surface of certain cells—including natural killer cells, macrophages, neutrophils, and mast cells—that contribute to the protective functions of the immune system. Fc receptors bind to antibodies that are attached to infected cells, invading pathogens, or cancer cells. Their activity stimulates phagocytic or cytotoxic cells to destroy microbes, infected cells, or cancer cells by antibody-mediated phagocytosis or ADCC. Some viruses such as flaviviruses use Fc receptors to help them infect cells, by a mechanism known as antibody-dependent enhancement of infection. Fc receptors are involved in ADCC process. For example, during ADCC FcγRIII receptors on the surface of natural killer (NK) cells stimulate the NK cells to release cytotoxic molecules from their granules to kill antibody-covered target cells.

There are several different types of Fc receptors, which are classified based on the type of antibody that they recognize. One group of IgG Fc receptors, FcγRs belong to the immunoglobulin superfamily and are the most important Fc receptors for inducing phagocytosis of opsonized (coated) microbes. They are expressed on leukocytes and are composed of 3 distinct classes: FcγRI, FcγRII (FcγRIIa and FcγRIIb), FcγRIII (FcγRIIIa and FcγRIIIb). The receptors are also distinguished by their affinity for IgG. FcγRI exhibits high affinity for IgG, whereas FcγRII and FcγRIII show a weaker affinity. FcγRIIa and FcγRIIIa are activating FcγRs which are expressed on monocytes/macrophages and monocytes/macrophages/NK cells, respectively, and can trigger cytotoxicity of human targets.

Two functional FcγR gene polymorphisms, FcγR3a-V158F and FcγR2a-H131R, have been identified that affect the binding of IgG, changing ADCC function and affecting clinical tumor response. FcγR2a-H131R polymorphism is located at the extracellular ligand-binding domain. It either has a histidine (H) or arginine (R) allele at amino acid position 131. The FcγR2a-131H/H genotype has a higher affinity to human IgG2 in an in vitro assay. FcγR3a-V158F polymorphism encodes either a valine (V) or phenylalanine (F) at amino acid position 158. In vitro studies have shown that FcγR3a V allele has a higher binding affinity to human IgG1 than the F allele, indicating immune effector cells bearing FcγR3a V allele mediate ADCC more effectively (Zhang et al. J. of Clinical Oncology, 25: 3712-3718, 2007).

A further need exists to improve the therapeutic effectiveness of monoclonal antibodies. There is a need to enhance effector function of antibodies, for example enhancing the ADCC and/or CDC function of antibodies.

Throughout this description, including the foregoing description of related art, any and all publicly available documents described herein, including any and all U.S. patents, are specifically incorporated by reference herein in their entirety. The foregoing description of related art is not intended in any way as an admission that any of the documents described therein, including pending United States patent applications, are prior art to embodiments of the present disclosure. Moreover, the description herein of any disadvantages associated with the described products, methods, and/or apparatus, is not intended to limit the disclosed embodiments. Indeed, embodiments of the present disclosure may include certain features of the described products, methods, and/or apparatus without suffering from their described disadvantages.

SUMMARY OF THE DISCLOSURE

The present disclosure relates to methods of enhancing the ADCC activity of therapeutic antibodies in the treatment of cellular diseases such as cancer and immune cell mediated diseases or disorders. In general, the ADCC activity of therapeutic antibodies may be enhanced by the co-administration of the therapeutic antibody with an ADCC enhancer molecule, with the formula I:

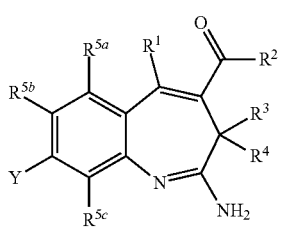

wherein

Y is an aryl ring substituted with C(=O)R8, and wherein said aryl ring is optionally further substituted with one or more substituents independently selected from F, Cl, CF3, CF3O—, HCF2O—, C1-C6 alkyl, C1-C6 heteroalkyl and ArO—;

R1, R3 and R4 are independently selected from H, C1-C6 alkyl, C2-C6 alkenyl, C2-C6 alkynyl, C1-C6 heteroalkyl, C3-C6 cycloalkyl, C3-C6 cycloalkenyl, heterocycloalkyl with 3 to 8 ring atoms wherein one atom is selected from nitrogen, oxygen and sulfur, aryl and 5-7 membered heteroaryl, wherein said alkyl, alkenyl, alkynyl, heteroalkyl, cycloalkyl, cycloalkenyl, heterocycloalkyl, aryl and heteroaryl are optionally substituted with one or more substituents independently selected from C1-C6 alkyl, C2-C6 alkenyl, C2-C6 alkynyl, F, Cl, Br, I, CN, OR6, NR6R7, C(=O)R6, C(=O)OR6, OC(=O)R6, C(=O)NR6R7, (C1-C6 alkyl)amino, CH3OCH2O—, R6OC(=O)CH=CH—, NR6SO2R7, SR64SO2R6;

or R3 and R4 together with the atom to which they are attached form a saturated or partially unsaturated C3-C6 carbocyclic ring, wherein said carbocyclic ring is optionally substituted with one or more substituents independently selected from C1-C6 alkyl, C2-C6 alkenyl, C2-C6 alkynyl, F, Cl, Br, I, CN, OR6, NR6R7, C(=O)R6, C(=O)OR6, OC(=O)R6, C(=O)NR6R7, (C1-C6 alkyl)amino, CH3OCH2O—, R6OC(=O)CH=CH—, NR6SO2R7, SR6 and SO2R6;

R2 and R8 are independently selected from H, OR6, NR6R7, C1-C6 alkyl, C2-C6 alkenyl, C2-C6 alkynyl, C1-C6 heteroalkyl, C3-C6 cycloalkyl, C3-C6 cycloalkenyl, heterocycloalkyl with 3 to 8 ring atoms wherein one atom is selected from nitrogen, oxygen and sulfur, aryl and 5-7 membered heteroaryl, wherein said alkyl, alkenyl, alkynyl, heteroalkyl, cycloalkyl, cycloalkenyl, heterocycloalkyl, aryl and heteroaryl are optionally substituted with one or more substituents independently selected from a C1-C6 alkyl, C2-C6 alkenyl, C2-C6 alkynyl, F, Cl, Br, I, CN, OR6, NR6R7, C(=O)R6, C(=O)OR6, OC(=O)R6, C(=O) NR6R7, (C1-C6alkyl)amino, CH3OCH2O—, R6OC(=O) CH=CH—, NR6SO2R7, SR6 and SO2R6;

R5a, R5b and R5c are independently selected from H, F, Cl, Br, I, OMe, CH3, CH2F, CHF2 and CF3 and R6 and R7 are independently selected from H, C1-C6 alkyl, C2-C6 alkenyl, C2-C6 alkynyl, C1-C6 heteroalkyl, C3-C6 cycloalkyl, C3-C6 cycloalkenyl, heterocycloalkyl with 3 to 8 ring atoms wherein one atom is selected from nitrogen, oxygen and sulfur, aryl and 5-7 membered heteroaryl, wherein said alkyl, alkenyl, alkynyl, heteroalkyl, cycloalkyl, cycloalkenyl, heterocycloalkyl, aryl and heteroaryl are optionally substituted with one or more substituents independently selected from C1-C6 alkyl, C2-C6 alkenyl, C2-C6 alkynyl, F, Cl, Br, I, CN, O-Alkyl, NH2, —C(=O)Alkyl, C(=O)H, C(=O)OH, C(=O)OAlkyl, OC(=O)H, OC(=O)Alkyl, (C1-C6alkyl)amino, (C1-C6alkyl)2amino CH3OCH2O—, and Alkyl-OC(=O) CH=CH—, or R6 and R7 together with the atom to which they are attached form a saturated or partially unsaturated heterocyclic ring with 3 to 8 ring atoms wherein one atom is selected from nitrogen, oxygen and sulfur, wherein said heterocyclic ring is optionally substituted with one or more substituents independently selected from C1-C6 alkyl, C2-C6 alkenyl, C2-C6 alkynyl, F, Cl, Br, I, CN, OR6, NH2, —C(=O)Alkyl, C(=O)H, C(=O)OH, C(=O)OAlkyl, OC(=O)H, OC(=O)Alkyl, (C1-C6alkyl)amino, (C1-C6alkyl)2amino CH3OCH2O—, and Alkyl-OC(=O)CH=CH—.

The invention also relates to a metabolite, solvate, tautomer or pharmaceutically acceptable salt of a compound according to formula I.

For example, R2 is OR6.

For example, R6 is C1-C6 alkyl, such as ethyl.

For example, the invention relates to a compound of formula I, where R2 is NR6R7.

For example, the invention relates to a compound of formula I, where R2 is NR6R7 and R6 and R7 are independently selected from H, C1-C6 alkyl and C1-C6 heteroalkyl, such as, for example, R6 and R7 are H, ethyl, propyl or CH2CH2OCH3.

For example, the invention relates to a compound of formula I, where Y is phenyl.

For example, the invention relates to a compound of formula I, where R8 is selected from OR6, NR6R7 and heterocycloalkyl with 3 to 8 ring atoms wherein one atom is selected from nitrogen, oxygen and sulfur For example, the invention relates to a compound of formula I, where R8 is heterocycloalkyl with 5 or 6 ring atoms wherein one atom is selected from nitrogen, oxygen and sulfur. For example, R8 is pyrrolidine.

For example, the invention relates to a compound of formula I, where R6 and R7 are independently selected from H and C1-C6 alkyl.

For example, the invention relates to a compound of formula I, where Y is

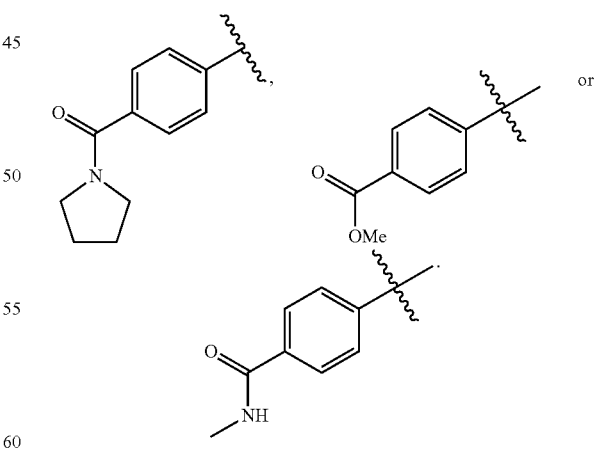

In some compounds of the invention, each of R1, R3, R4, R5a, R5b and R5c is hydrogen.

For example, the invention relates to a compound selected from
(1E,4E)-ethyl-2-amino-8-(4-pyrrolidine-1-carbonyl)phenyl)-3H-benzo[b]azepine-4-carboxylate;

(1E,4E)-ethyl-2-amino-8-(4-(methoxycarbonyl)phenyl)-3H-benzo[b]azepine-4-carboxylate;
(1E,4E)-ethyl-2-amino-8-(4-(methylcarbamoyl)phenyl)-3H-benzo[b]azepine-4-carboxylate;
(1E,4E)-2-amino-N,N-dipropyl-8-(4-(pyrrolidine-1-carbonyl)phenyl)-3H-benzo[b]azepine-4-carboxamide
and pharmaceutically acceptable salts thereof.

In a preferred embodiment, the ADCC enhancer molecule of the present invention is {2-amino-8-[4-(pyrrolidinylcarbonyl)phenyl]-(3H-benzo[f]azepin-4-yl)}-N,N-dipropylcarboxamide, with the chemical structure as follows:

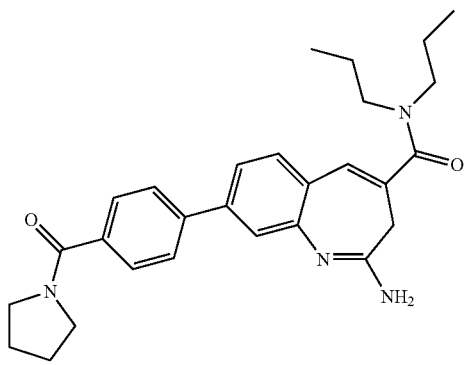 [SMILES: CCCN(CCC)C(=O)C1=Cc2ccc(-c3ccc(C(=O)N4CCCC4)cc3)cc2N=C(N)C1]

The ADCC enhancer molecule enhances or improves the effector activity of an antibody. Thus, regardless of the antigen-binding activity, the methods of the present invention can increase the therapeutic effect of an antibody by enhancing the effector activity exhibited by the antibody. The ADCC enhancer molecule may improve ADCC by activating NK cells or $CD56^+$ cells either directly or indirectly. Additionally, having a greater proportion of activated NK cells may help overcome the poor ADCC observed in a subset of patients that have low affinity Fc receptors.

Therapeutic MAbs capable of ADCC are preferred. These include anti-CD20 rituximab (Rituxan®), anti-Her2 trastuzumab (Herceptin®), anti-EGFR cetuximab (Erbitux®), and anti-EGFR panitumumab (Vectibix®).

According to some embodiments, methods are provided for increasing ADCC in a subject receiving therapeutic monoclonal antibody treatment. In some embodiments, the method comprises administering to a subject a therapeutically effective amount of a therapeutic antibody and an ADCC enhancer molecule in an amount sufficient to increase ADCC. Alternatively, the method of the present invention comprises administering to a subject a therapeutically effective amount of a therapeutic antibody, an ADCC enhancer molecule in an amount sufficient to increase ADCC and one or more chemotherapeutic agents.

According to some embodiments, methods are provided for enhancing the killing of NK sensitive target cells. In some embodiments, the method comprises administering to subject a therapeutically effective amount of a therapeutic antibody and an ADCC enhancer molecule in an amount sufficient to increase killing of NK sensitive target cells.

According to some embodiments, methods are provided for enhancing the effector activity of NK cells or $CD56^+$ cells. In some embodiments, the method comprises administering to subject a therapeutically effective amount of a therapeutic antibody and an ADCC enhancer molecule in an amount sufficient to increase effector activity of NK cells or $CD56^+$ cells.

According to some embodiments, methods are provided for enhancing ADCC in cells of patients. In some embodiments, the method comprises administering to subject a therapeutically effective amount of a therapeutic antibody and an ADCC enhancer molecule in an amount sufficient to increase ADCC. The subjects that may otherwise not be good therapeutic candidates for MAb therapy because they express only low levels of tumor antigens against which the monoclonal antibody is directed or because they have single nucleotide polymorphisms in their Fc receptors which lower their affinity for the monoclonal antibody.

According to some embodiments, methods are provided for enhancing the therapeutic effectiveness of monoclonal antibodies. According to some embodiments, methods are provided for increasing the efficiency of a therapeutic monoclonal antibody. In some embodiments the method comprises administering to subject a therapeutically effective amount of a therapeutic antibody and an ADCC enhancer molecule in an amount sufficient to increase ADCC. Alternatively, the method of the present invention comprises administering to a subject a therapeutically effective amount of a therapeutic antibody, an ADCC enhancer molecule in an amount sufficient to increase ADCC and one or more chemotherapeutic agents.

According to some embodiments, methods are provided for increasing the clinical effectiveness of a therapeutic anti-ErbB2 monoclonal antibody comprising administering to a subject in need thereof the therapeutic anti-ErbB2 monoclonal antibody in combination with the ADCC enhancer molecule of the present invention. Alternatively, the method of the present invention comprises administering to a subject in need thereof the therapeutic anti-ErbB2 monoclonal antibody in combination with the ADCC enhancer molecule of the present invention and one or more chemotherapeutic agents. In preferred embodiments, the anti-ErbB2 monoclonal is trastuzumab.

According to some embodiments, methods are provided for treating breast cancer comprising administering to a subject in need thereof a therapeutic anti-ErbB2 monoclonal antibody in combination with the ADCC enhancer molecule of the present invention. Alternatively, the method of the present invention comprises administering to a subject in need thereof a therapeutic anti-ErbB2 monoclonal antibody in combination with the ADCC enhancer molecule of the present invention and one or more chemotherapeutic agents. In preferred embodiments, the anti-ErbB2 monoclonal is trastuzumab.

According to some embodiments, methods are provided for increasing the clinical effectiveness of a therapeutic anti-CD20 monoclonal antibody comprising administering to a subject in need thereof the therapeutic anti-CD20 monoclonal antibody in combination with the ADCC enhancer molecule of the present invention. In preferred embodiments, the anti-CD20 monoclonal is rituximab.

According to some embodiments, methods are provided for treating a B-cell disorder comprising administering to a subject in need thereof a therapeutic anti-CD20 monoclonal antibody in combination with the ADCC enhancer molecule of the present invention. In preferred embodiments, the anti-CD20 monoclonal is rituximab. In some embodiments, the B-cell disorder is lymphoma, leukemia, or rhuematoid arthritis.

According to some embodiments, methods are provided for increasing the clinical effectiveness of a therapeutic anti-EGFR monoclonal antibody comprising administering to a subject in need thereof the therapeutic anti-EGFR monoclonal antibody in combination with the ADCC enhancer molecule of the present invention. The methods of the present invention also comprises administering to a subject in need thereof the therapeutic anti-EGFR monoclonal antibody in combination with the ADCC enhancer molecule of the present invention and one or more chemotherapeutic agents. In preferred embodiments, the anti-EGFR monoclonal is panitumumab, cetuximab, necitumumab, or zalutumumab.

According to some embodiments, methods are provided for treating EGFR-expressing, metastatic colorectal carcinoma comprising administering to a subject in need thereof a therapeutic anti-EGFR monoclonal antibody in combination with the ADCC enhancer molecule of the present invention. According to some embodiments, methods are provided for treating EGFR-expressing, head and neck cancer comprising administering to a subject in need thereof a therapeutic anti-EGFR monoclonal antibody in combination with the ADCC enhancer molecule of the present invention. The present invention also includes methods of treating EGFR-expressing, metastatic colorectal carcinoma comprising administering to a subject in need thereof a therapeutic anti-EGFR monoclonal antibody in combination with the ADCC enhancer molecule of the present invention and one or more chemotherapeutic agents. According to some embodiments, methods are also provided for treating EGFR-expressing, head and neck cancer comprising administering to a subject in need thereof a therapeutic anti-EGFR monoclonal antibody in combination with the ADCC enhancer molecule of the present invention and one or more chemotherapeutic agents. In preferred embodiments, the anti-EGFR monoclonal is panitumumab, cetuximab, necitumumab, or zalutumumab.

According to some embodiments, methods are provided for treating KRAS mutant colorectal cancer comprising administering to a subject in need thereof a therapeutic monoclonal antibody in combination with the ADCC enhancer molecule of the present invention. In preferred embodiments, the therapeutic monoclonal antibody is panitumumab or cetuximab.

According to some embodiments, methods are provided for treating cancer comprising administering to a subject in need thereof a therapeutically effective amount of a therapeutic antibody and an ADCC enhancer molecule in an amount sufficient to increase ADCC. The present invention also includes methods of treating cancer comprising administering to a subject in need thereof a therapeutically effective amount of a therapeutic antibody, an ADCC enhancer molecule in an amount sufficient to increase ADCC and one or more chemotherapeutic agents.

According to some embodiments, methods are provided for treating a B-cell malignancy or B-cell disorder comprising administering to a subject in need thereof a therapeutically effective amount of a therapeutic antibody and an ADCC enhancer molecule in an amount sufficient to increase ADCC.

According to some embodiments, methods are provided for treating an autoimmune disorder comprising administering to a subject in need thereof a therapeutically effective amount of a therapeutic antibody and an ADCC enhancer molecule in an amount sufficient to increase ADCC. In some embodiments, the autoimmune disorder is rheumatoid arthritis.

According to some embodiments, methods are provided for avoiding a tumor relapse in a subject comprising administering to a subject in need thereof a therapeutically effective amount of a therapeutic antibody and an ADCC enhancer molecule in an amount sufficient to increase ADCC.

In some embodiments, the therapeutic antibodies have a murine, human or non human primate IgG1 or an IgG3 Fc portion. In some embodiments, the therapeutic antibody is a chimeric, human or humanized antibody or a fragment thereof.

In the present invention, methods are provided for selecting an appropriate therapeutic regimen for a subject in need thereof comprising determining a SNP of FcgR3a at amino acid position 158, wherein a homozygous valine at amino acid position 158 of FcgR3a indicates the subject is predicted to be more responsive to the therapeutic regimen than a subject without the homozygous valine at amino acid position 158 of FcgR3a.

In this invention, methods are also provided for selecting an appropriate therapeutic regimen for a subject in need thereof comprising determining a SNP of FcgR2a at amino acid position 131, wherein a homozygous histidine at amino acid position 131 of FcgR2a indicates the subject is predicted to be more responsive to the therapeutic regimen than a subject without the homozygous histidine at amino acid position 131 of FcgR2a.

The present invention provides a pharmaceutical pack or kit comprising one or more containers filled with a liquid or lyophilized ADCC enhancer molecule, optionally a therapeutic antibody, and/or one or more chemotherapeutic agents.

DETAILED DESCRIPTION OF THE INVENTION

Figure 1:
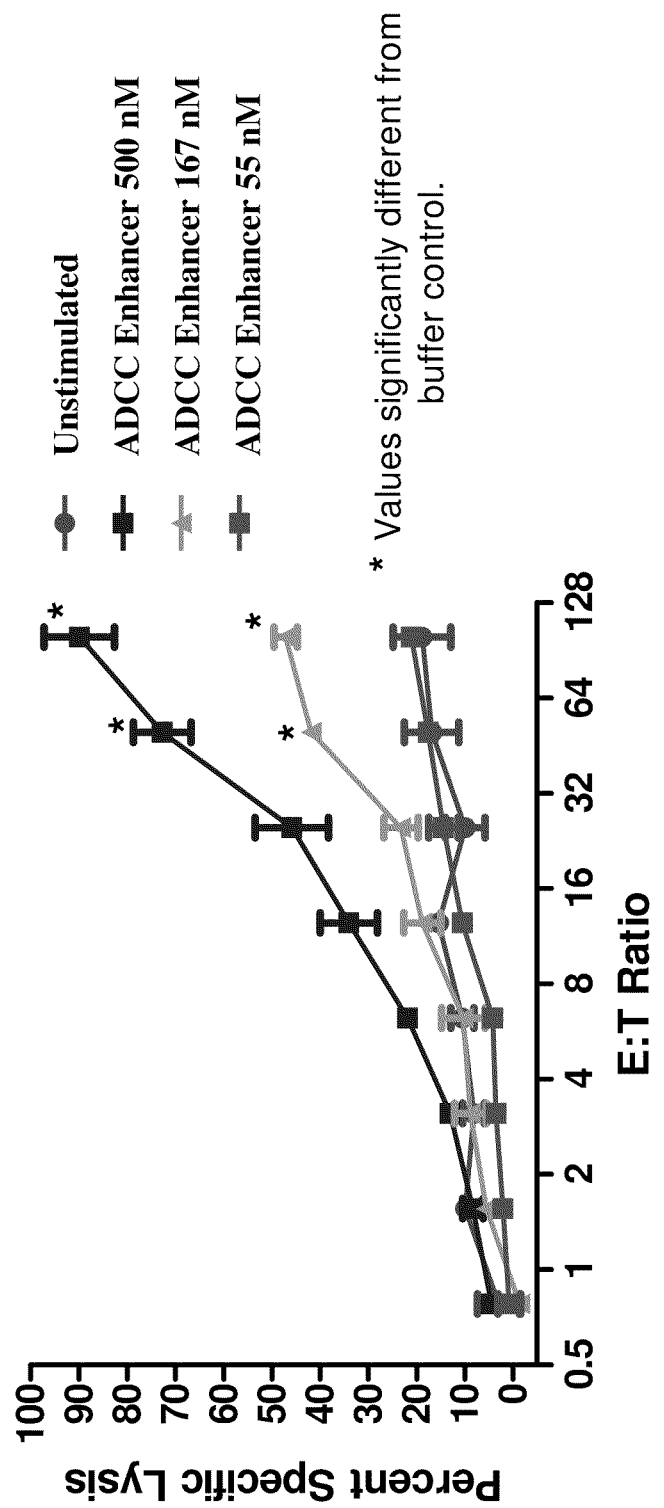
FIG. 1 is a line graph showing the lysis of K562 target cells. Calcein AM labeled K562 target cells were incubated with PBMC effector cells that had been previously stimulated with the ADCC enhancer. Percent specific lysis of target cells was evaluated over a range of effector:target cell ratios.

The invention is bases upon the discovery that an ADCC enhancer molecule increases the antibody-dependent cellular cytotoxicity (ADCC) activity of antibodies. Accordingly, the invention provides methods of treating cellular diseases such as cancer and immune cell mediated diseases or disorders by administering a therapeutic monoclonal antibody and an ADCC enhancer molecule, a compound with formula I as follows:

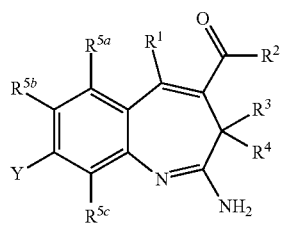

wherein,

Y is an aryl ring substituted with C(=O)R8, and wherein said aryl ring is optionally further substituted with one or more substituents independently selected from F, Cl, CF3, CF3O—, HCF2O—, C1-C6 alkyl, C1-C6 heteroalkyl and ArO—;

R1, R3 and R4 are independently selected from H, C1-C6 alkyl, C2-C6 alkenyl, C2-C6 alkynyl, C1-C6 heteroalkyl, C3-C6 cycloalkyl, C3-C6 cycloalkenyl, heterocycloalkyl with 3 to 8 ring atoms wherein one atom is selected from nitrogen, oxygen and sulfur, aryl and 5-7 membered heteroaryl, wherein said alkyl, alkenyl, alkynyl, heteroalkyl, cycloalkyl, cycloalkenyl, heterocycloalkyl, aryl and heteroaryl are optionally substituted with one or more substituents independently selected from C1-C6 alkyl, C2-C6 alkenyl, C2-C6 alkynyl, F, Cl, Br, I, CN, OR6, NR6R7, C(=O)R6, C(=O)OR6, OC(=O)R6, C(=O)NR6R7, (C1-C6 alkyl)amino, CH3OCH2O—, R6OC(=O)CH=CH—, NR6SO2R7, SR64SO2R6;

or R3 and R4 together with the atom to which they are attached form a saturated or partially unsaturated C3-C6 carbocyclic ring, wherein said carbocyclic ring is optionally substituted with one or more substituents independently selected from C1-C6 alkyl, C2-C6 alkenyl, C2-C6 alkynyl, F, Cl, Br, I, CN, OR6, NR6R7, C(=O)R6, C(=O)OR6, OC(=O)R6, C(=O)NR6R7, (C1-C6 alkyl)amino, CH3OCH2O—, R6OC(=O)CH=CH—, NR6SO2R7, SR6 and SO2R6;

R2 and R8 are independently selected from H, OR6, NR6R7, C1-C6 alkyl, C2-C6 alkenyl, C2-C6 alkynyl, C1-C6 heteroalkyl, C3-C6 cycloalkyl, C3-C6 cycloalkenyl, heterocycloalkyl with 3 to 8 ring atoms wherein one atom is selected from nitrogen, oxygen and sulfur, aryl and 5-7 membered heteroaryl, wherein said alkyl, alkenyl, alkynyl, heteroalkyl, cycloalkyl, cycloalkenyl, heterocycloalkyl, aryl and heteroaryl are optionally substituted with one or more substituents independently selected from a C1-C6 alkyl, C2-C6 alkenyl, C2-C6 alkynyl, F, Cl, Br, I, CN, OR6, NR6R7, C(=O)R6, C(=O)OR6, OC(=O)R6, C(=O)NR6R7, (C1-C6alkyl)amino, CH3OCH2O—, R6OC(=O)CH=CH—, NR6SO2R7, SR6 and SO2R6;

R5a, R5b and R5c are independently selected from H, F, Cl, Br, I, OMe, CH3, CH2F, CHF2 and CF3 and R6 and R7 are independently selected from H, C1-C6 alkyl, C2-C6 alkenyl, C2-C6 alkynyl, C1-C6 heteroalkyl, C3-C6 cycloalkyl, C3-C6 cycloalkenyl, heterocycloalkyl with 3 to 8 ring atoms wherein one atom is selected from nitrogen, oxygen and sulfur, aryl and 5-7 membered heteroaryl, wherein said alkyl, alkenyl, alkynyl, heteroalkyl, cycloalkyl, cycloalkenyl, heterocycloalkyl, aryl and heteroaryl are optionally substituted with one or more substituents independently selected from C1-C6 alkyl, C2-C6 alkenyl, C2-C6 alkynyl, F, Cl, Br, I, CN, O-Alkyl, NH2, —C(=O)Alkyl, C(=O)H, C(=O)OH, C(=O)OAlkyl, OC(=O)H, OC(=O)Alkyl, (C1-C6alkyl)amino, (C1-C6alkyl)2amino CH3OCH2O—, and Alkyl-OC(=O)CH=CH—, or R6 and R7 together with the atom to which they are attached form a saturated or partially unsaturated heterocyclic ring with 3 to 8 ring atoms wherein one atom is selected from nitrogen, oxygen and sulfur, wherein said heterocyclic ring is optionally substituted with one or more substituents independently selected from C1-C6 alkyl, C2-C6 alkenyl, C2-C6 alkynyl, F, Cl, Br, I, CN, OR6, NH2, —C(=O)Alkyl, C(=O)H, C(=O)OH, C(=O)OAlkyl, OC(=O)H, OC(=O)Alkyl, (C1-C6alkyl)amino, (C1-C6alkyl)2amino CH3OCH2O—, and Alkyl-OC(=O)CH=CH—.

The invention also relates to a metabolite, solvate, tautomer or pharmaceutically acceptable salt of a compound according to formula I.

For example, R2 is OR6.

For example, R6 is C1-C6 alkyl, such as ethyl.

For example, the invention relates to a compound of formula I, where R2 is NR6R7.

For example, the invention relates to a compound of formula I, where R2 is NR6R7 and R6 and R7 are independently selected from H, C1-C6 alkyl and C1-C6 heteroalkyl, such as, for example, R6 and R7 are H, ethyl, propyl or CH2CH2OCH3.

For example, the invention relates to a compound of formula I, where Y is phenyl.

For example, the invention relates to a compound of formula I, where R8 is selected from OR6, NR6R7 and heterocycloalkyl with 3 to 8 ring atoms wherein one atom is selected from nitrogen, oxygen and sulfur For example, the invention relates to a compound of formula I, where R8 is heterocycloalkyl with 5 or 6 ring atoms wherein one atom is selected from nitrogen, oxygen and sulfur. For example, R8 is pyrrolidine.

For example, the invention relates to a compound of formula I, where R6 and R7 are independently selected from H and C1-C6 alkyl.

For example, the invention relates to a compound of formula I, where Y is

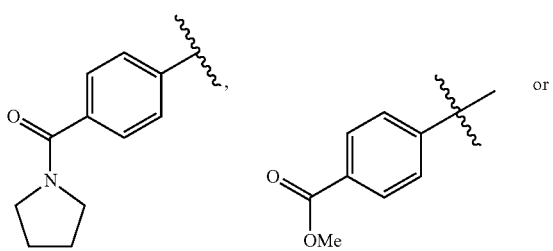

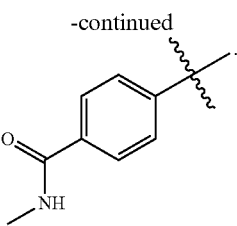

In some compounds of the invention, each of R1, R3, R4, R5a, R5b and R5c is hydrogen.

For example, the invention relates to a compound selected from (1E,4E)-ethyl-2-amino-8-(4-pyrrolidine-1-carbonyl)phenyl)-3H-benzo[b]azepine-4-carboxylate;

(1E,4E)-ethyl-2-amino-8-(4-(methoxycarbonyl)phenyl)-3H-benzo[b]azepine-4-carboxylate;

(1E,4E)-ethyl2-amino-8-(4-(methylcarbamoyl)phenyl)-3H-benzo[b]azepine-4-carboxylate;

(1E,4E)-2-amino-N,N-dipropyl-8-(4-(pyrrolidine-1-carbonyl)phenyl)-3H-benzo[b]azepine-4-carboxamide and pharmaceutically acceptable salts thereof. Other suitable ADCC enhancers are described in WO2007/024612, the contents of which are hereby incorporated by reference in its entirety.

In a preferred embodiment, the ADCC enhancer molecule of the present invention is {2-amino-8-[4-(pyrrolidinylcarbonyl)phenyl]-(3H-benzo[f]azepin-4-yl)}-N,N-dipropylcarboxamide with the chemical structure as follows:

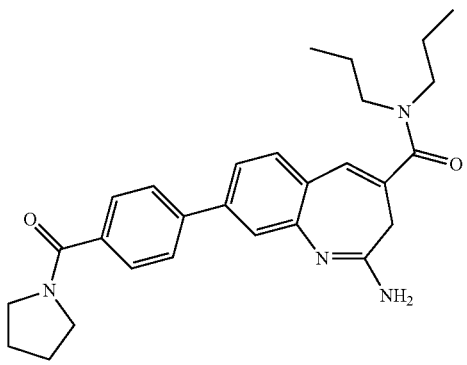 [SMILES: CCCN(CCC)C(=O)C1=Cc2ccc(-c3ccc(C(=O)N4CCCC4)cc3)cc2N=C(N)C1]

The ADCC enhancer molecule enhances or improves the effector activity of an antibody. Thus, regardless of the antigen-binding activity, the methods of the present invention can increase the therapeutic effect of an antibody by enhancing the effector activity exhibited by the antibody. Thus, the methods of the invention are generally useful for treating or alleviating a symptom of any disorder in which enhanced antibody effector activity is desired in a subject in need thereof. The ADCC enhancer molecule may improve ADCC by activating NK cells or CD56$^+$ cells either directly or indirectly. Additionally, having a greater proportion of activated NK cells may help overcome the poor ADCC observed in a subset of patients that have low affinity Fc receptors.

A subject in need thereof includes cancer subjects that have been identified as having a KRAS mutation or an FcγR polymorphism, or previously identified as being unresponsive to therapeutic antibody treatment or has impaired ADCC function.

In another embodiment, the ADCC enhancer molecule of the invention is administered in combination with one or more therapeutic antibodies. In some embodiments, the antibodies have in vivo therapeutic and/or prophylactic uses against cancer and other cellular diseases.

In certain embodiments, the ADCC enhancer molecule is administered prior to, concurrently with, or subsequent to the administration of the one or more therapeutic antibodies. In one embodiment, the ADCC enhancer molecule is formulated with one or more therapeutic antibodies. In another embodiment, the one or more therapeutic antibodies is administered in a separate pharmaceutical composition. In accordance with this embodiment, the one or more therapeutic antibodies may be administered to a subject by the same or different routes of administration as those used to administer ADCC enhancer molecule.

In another aspect, the invention provides a method for killing a cancer cell comprising administering an amount of an ADCC enhancer molecule of the present invention in combination with a therapeutic monoclonal antibody to kill a cancer cell. The types of therapeutic monoclonal antibodies include, but are not limited to, rituximab, cetuximab, panitumumab, and trastuzumab.

Therapeutic Antibodies

Within the context of this invention, the term "therapeutic antibody or antibodies" designates more specifically any antibody that functions to deplete target cells in a patient. Specific examples of such target cells include tumor cells, virus-infected cells, allogenic cells, pathological immunocompetent cells (e.g., B lymphocytes, T lymphocytes, antigen-presenting cells, etc.) involved in cancers, allergies, autoimmune diseases, allogenic reactions. Most preferred target cells within the context of this invention are tumor cells and virus-infected cells. The therapeutic antibodies may, for instance, mediate a cytotoxic effect or cell lysis, particularly by antibody-dependant cell-mediated cytotoxicity (ADCC).

ADCC requires leukocyte receptors for the Fc portion of IgG (FcγR) whose function is to link the IgG-sensitized antigens to FcγR-bearing cytotoxic cells and to trigger the cell activation machinery. While this mechanism of action has not been evidenced in vivo in humans, it may account for the efficacy of such target cell-depleting therapeutic antibodies. Therefore, the therapeutic antibody is capable of forming an immune complex. For example, an immune complex can be a tumoral target covered by therapeutic antibodies. The therapeutic antibodies may by polyclonal or, preferably, monoclonal. They may be produced by hybridomas or by recombinant cells engineered to express the desired variable and constant domains. The antibodies may be single chain antibodies or other antibody derivatives retaining the antigen specificity and the lower hinge region or a variant thereof. These may be polyfunctional antibodies, recombinant antibodies, humanized antibodies, fragments or variants thereof. Said fragment or a derivative thereof is preferably selected from a Fab fragment, a Fab'2 fragment, a CDR and a ScFv. Therapeutic antibodies are specific for surface antigens, e.g., membrane antigens. Most preferred therapeutic antibodies are specific for tumor antigens (e.g., molecules specifically expressed by tumor cells), such as CD20, CD52, ErbB2 (or HER2/Neu), CD33, CD22, CD25, MUC-1, CEA, KDR, αVβ33, particularly lymphoma antigens (e.g., CD20). The therapeutic antibodies have preferably human or non human primate IgG1 or IgG3 Fc portion, more preferably human IgG1.

Typical examples of therapeutic antibodies of this invention are rituximab, cetuximab, panitumumab, and trastuzumab. Such antibodies may be used according to clinical protocols that have been authorized for use in human subjects. Additional specific examples of therapeutic antibodies include, for instance, alemtuzumab, epratuzumab, basiliximab, daclizmab, labetuzumab, seviumab, tuvurimab, palivizumab, infliximab, omalizumab, efalizuab, natalizumab, and clenoliximab. One skilled in the art would recognize that other therapeutic antibodies are useful in the methods of the invention.

In some embodiments, the dose for the therapeutic antibody is preferably between 200-600 mg/m$^2$. This includes 200 mg/m$^2$, 250 mg/m$^2$, 300 mg/m$^2$, 350 mg/m$^2$, 400 mg/m$^2$, 450 mg/m$^2$, 500 mg/m$^2$, 600 mg/m$^2$ and points in-between. Preferably, the therapeutic antibody is administered by intravenous infusion (e.g., as a 30 min., 45 min., 60 min., 90 min, or 120 min infusion). For example, the dose of the therapeutic antibody may be 400 mg/m$^2$ administered as a 120-minute intravenous infusion (e.g., maximum infusion rate 10 mg/min).

In some embodiments, the dose for the therapeutic antibody is preferably between 1-10 mg/kg. This includes 1 mg/kg, 2 mg/kg, 3 mg/kg, 4 mg/kg, 5 mg/kg, 6 mg/kg, 7 mg/kg, 8 mg/kg and points in-between. Preferably, the therapeutic antibody is administered by intravenous infusion (e.g., as a 30 min., 45 min., 60 min., 90 min, or 120 min infusion). For example, the dose of the therapeutic antibody may be 6 mg/kg administered as a 30-, 60-, or 90-minute intravenous infusion.

ERBITUX® (Cetuximab)

In some embodiment the therapeutic antibody is an anti-EGFR (epidermal growth factor receptor) monoclonal antibody. In some embodiment the therapeutic antibody is a human or humanized anti-EGFR monoclonal antibody. In some embodiment the therapeutic antibody is a chimeric anti-EGFR monoclonal antibody. Preferably, the monoclonal antibody is ERBITUX® (cetuximab), a chimeric (mouse/human) monoclonal antibody and epidermal growth factor receptor (EGFR) inhibitor.

Cetuximab may be used in combination with the ADCC enhancer of the present invention for the treatment of metastatic colorectal cancer and head and neck cancer. Colorectal cancer includes the well-accepted medical definition that defines colorectal cancer as a medical condition characterized by cancer of cells of the intestinal tract below the small intestine (i.e. the large intestine (colon), including the cecum, ascending colon, transverse colon, descending colon, and sigmoid colon, and rectum). In some embodiments, the ADCC enhancer molecule is used in combination with cetuximab for the treatment of EGFR-expressing metastatic colorectal carcinoma. In some embodiments, the ADCC enhancer molecule is used in combination with cetuximab for the treatment of EGFR-expressing metastatic colorectal carcinoma in patients who are refractory to irinotecan-based chemotherapy.

The head and neck section is an assembly of a plurality of organs, and the primary foci of head and neck cancer include the paranasal sinus, the epipharynx, the oropharynx, the oral cavity, the hypopharynx, the larynx, and the salivary glands. Head and neck cancer includes cancers of the head or neck region of the body. Most head and neck cancers are squamous cell carcinomas, but some may be exophilic or endophilic. Examples of head and neck cancers include but are not limited to the lip, oral cavity (mouth), tongue, throat, trachea, nasal cavity, paranasal sinuses, pharynx, larynx, thyroid, salivary glands and cervical lymph nodes of the neck, and the like.

In some embodiments, the ADCC enhancer molecule is used in combination with cetuximab for the treatment of locally or regionally advanced squamous cell carcinoma of the head and neck. In some embodiments, the ADCC enhancer molecule is used in combination with cetuximab for the treatment of recurrent or metastatic squamous cell carcinoma of the head and neck progressing after platinum-based therapy.

According to some embodiments, the invention provides methods of increasing the effectiveness of cetuximab in the treatment of metastatic colorectal cancer or head and neck cancer. Thus, some embodiments provide a method for increasing the clinical effectiveness of cetuximab comprising administering to a subject in need thereof cetuximab in combination with the ADCC enhancer molecule of the present invention.

The dose for cetuximab is preferably between 200-600 mg/m$^2$. This includes 200 mg/m$^2$, 250 mg/m$^2$, 300 mg/m$^2$, 350 mg/m$^2$, 400 mg/m$^2$, 450 mg/m$^2$, 500 mg/m$^2$, 600 mg/m$^2$ and points in-between. Preferably, cetuximab is administered by intravenous infusion (e.g., as a 30 min., 45 min., 60 min., 90 min, or 120 min infusion). For example, the dose of cetuximab may be 400 mg/m$^2$ administered as a 120-minute intravenous infusion (e.g., maximum infusion rate 10 mg/min).

Cetuximab may be administered with a higher initial dose followed by lower subsequent doses. The frequency of administration is preferably one time weekly. For example, following an initial dose of cetuximab at 400 mg/m$^2$ administered as a 120-minute intravenous infusion (e.g., maximum infusion rate 10 mg/min), subsequent weekly doses may be at 250 mg/m$^2$ infused over 60 minutes (e.g., maximum infusion rate 10 mg/min) until disease progression or unacceptable toxicity.

HERCEPTIN® (Trastuzumab)

In some embodiment the therapeutic antibody is an anti-ErbB2 (HER2/neu) monoclonal antibody. In some embodiment the therapeutic antibody is a human or humanized anti-ErbB2 monoclonal antibody. In some embodiment the therapeutic antibody is a chimeric anti-ErbB2 monoclonal antibody.

In some embodiments, the therapeutic antibody is HERCEPTIN® (trastuzumab), a humanized monoclonal antibody that interferes with the human epidermal growth factor receptor 2 (HER2/neu receptor). HER2/neu receptor is a member of the ErbB protein family, more commonly known as the epidermal growth factor receptor family. Trastuzumab reverses the effects of an overactive HER2 receptor.

In some embodiments, trastuzumab is administered in combination with the ADCC enhancer molecule of the present invention for the treatment of breast cancer. In some embodiments, the ADCC enhancer molecule is used in combination with cetuximab for the treatment of patients with metastatic breast cancer whose tumors overexpress the HER2 protein.

According to some embodiments, the invention provides methods of increasing the effectiveness of trastuzumab in the treatment of breast cancer. Thus, some embodiments provide a method for increasing the clinical effectiveness of trastuzumab comprising administering to a subject in need thereof trastuzumab in combination with the ADCC enhancer molecule of the present invention.

The dose for trastuzumab is preferably between 1-10 mg/kg. This includes 1 mg/kg, 2 mg/kg, 3 mg/kg, 4 mg/kg, 5 mg/kg, 6 mg/kg, 7 mg/kg, 8 mg/kg and points in-between. Preferably, trastuzumab is administered by intravenous infusion (e.g., as a 30 min., 45 min., 60 min., 90 min, or 120 min infusion). For example, the dose of trastuzumab may be 6 mg/kg administered as a 30-, 60-, or 90-minute intravenous infusion.

Trastuzumab may be administered with a higher initial dose followed by lower subsequent doses or maintenance dose. The frequency of administration is preferably one time weekly. For example, following an initial dose of trastuzumab at 4 mg/kg administered as a 90-minute intravenous infusion, subsequent weekly doses may be at 2 mg/kg infused over 30 minutes until disease progression or unacceptable toxicity.

RITUXAN® (Rituximab)

In some embodiment the therapeutic antibody is an anti-CD20 monoclonal antibody. In some embodiment the therapeutic antibody is a human or humanized anti-CD20 monoclonal antibody. In some embodiment the therapeutic antibody is a chimeric anti-CD20 monoclonal antibody.

Preferably, the monoclonal antibody against the protein CD20 is RITUXAN® (Rituximab). Thus, some embodiments provide a method for increasing the clinical effectiveness of trastuzumab comprising administering to a subject in need thereof trastuzumab in combination with the ADCC enhancer molecule of the present invention.

Rituximab may be used in combination with the ADCC enhancer of the present invention for the treatment of B-cell disorders, such as lymphomas, leukemias, and some autoimmune disorders (e.g., rhuematoid arthritis).

Rituximab destroys both normal and malignant B cells that have CD20 on their surfaces. Rituximab may be used in combination with the ADCC enhancer of the present invention to treat diseases which are characterized by having too many B cells, overactive B cells or dysfunctional B cells. According to some embodiments, the invention provides methods of increasing the effectiveness of rituximab in the treatment of B-cell disorders, such as lymphomas, leukemias, and some autoimmune disorders (e.g., rhuematoid arthritis). Thus, some embodiments provide a method of increasing the clinical effectiveness of rituximab comprising administering to a subject in need thereof rituximab in combination with the ADCC enhancer molecule of the present invention.

In some embodiments, rituximab may be used in combination with the ADCC enhancer of the present invention to treat hematological neoplasms such as leukemias and lymphomas.

Rituximab may be used in combination with the ADCC enhancer of the present invention to treat autoimmune diseases, including, but not limited to, idiopathic autoimmune hemolytic anemia, pure red cell aplasia, idiopathic thrombocytopenic purpura (ITP), Evans syndrome, vasculitis (for example Wegener's Granulomatosis), bullous skin disorders (for example pemphigus, pemphigoid), type 1 diabetes mellitus, Sjogren's syndrome, and Devic's disease.

According to some embodiments, rituximab may be used in combination with the ADCC enhancer of the present invention to treat hematological malignancies. Such hematological malignancies include, for example, B-cell lymphoma, acute myelogenous leukemia, and chronic lymphocytic leukemia. Such treatment results in, for example, tumor regression in an animal model or in a human. Tumor regression can include, for example, killing a cancer cell.

Accordingly, in one aspect the invention provides a method for killing a cancer cell comprising administering an amount rituximab and the ADCC enhancer of the present invention in amounts effective to kill a cancer cell of a hematopoietic cancer. The types of hematopoietic cancer include, but are not limited to, B cell lymphoma, chronic lymphocytic leukemia, and acute myelogenous leukemia.

In some embodiments, rituximab is administered in combination with the ADCC enhancer molecule of the present invention for the treatment of patients with relapsed or refractory, low-grade or follicular, CD20-positive, B-cell, non-Hodgkin's lymphoma.

In some embodiments, rituximab is administered in combination with the ADCC enhancer molecule of the present invention for the first-line treatment of follicular, CD20-positive, B-cell non-Hodgkin's lymphoma in combination with CVP chemotherapy.

In some embodiments, rituximab is administered in combination with the ADCC enhancer molecule of the present invention for the treatment rheumatoid arthritis. Methotrexate may further be added to the combination. Accordingly, Accordingly, in some embodiments, rituximab is administered in combination with the ADCC enhancer molecule of the present invention and with methotrexate to reduce signs and symptoms in adult patients with moderately- to severely-active rheumatoid arthritis. In some embodiments, rituximab is administered in combination with the ADCC enhancer molecule of the present invention and with methotrexate to reduce signs and symptoms in adult patients with moderately- to severely-active rheumatoid arthritis who have had an inadequate response to one or more TNF antagonist therapies.

The dose for rituximab is preferably between 200-1200 mg/m$^2$. This includes 200 mg/m$^2$, 250 mg/m$^2$, 300 mg/m$^2$, 350 mg/m$^2$, 375 mg/m$^2$, 400 mg/m$^2$, 450 mg/m$^2$, 500 mg/m$^2$, 600 mg/m$^2$ 700 mg/m$^2$, 800 mg/m$^2$, 900 mg/m$^2$, 1000 mg/m$^2$, 1100 mg/m$^2$, 1200 mg/m$^2$, and points in-between. Preferably, rituximab is administered by intravenous infusion (e.g., as a 30 min., 45 min., 60 min., 90 min, or 120 min infusion). For example, the dose of rituximab may be 375 mg/m$^2$ administered as a 120-minute intravenous infusion, preferably within 4 hours.

The frequency of administration of rituximab is preferably one time weekly or monthly and may continue until disease progression or unacceptable toxicity. In some embodiments, 2-16 does of rituximab is administered (e.g., 2, 4, 6, 8, 10, 12, 14, 16 doses). In some embodiments, rituximab is given at 375 mg/m$^2$ IV infusion once weekly for 4 or 8 doses. In some embodiments, administration of rituximab is 4 doses every 6 months for up to 16 doses. In some embodiments, rituximab is given as two-1000 mg IV infusions separated by 2 weeks.

VECTIBIX® (Panitumumab)

In some embodiments, the therapeutic antibody is Vectibix® (panitumumab). Vectibix® (panitumumab) is a recombinant, human IgG2 kappa monoclonal antibody that binds specifically to the human epidermal growth factor receptor (EGFR). Vectibix® is indicated as a single agent for the treatment of EGFR-expressing, metastatic colorectal carcinoma with disease progression on or following fluoropyrimidine-, oxaliplatin-, and irinotecan-containing chemotherapy regimens.

According to some embodiments, the invention provides methods of increasing the effectiveness of panitumumab in the treatment of EGFR-expressing, metastatic colorectal carcinoma. Thus, some embodiments provide a method for increasing the clinical effectiveness of panitumumab comprising administering to a subject in need thereof panitumumab in combination with the ADCC enhancer molecule of the present invention. Other embodiments provide a method for increasing the clinical effectiveness of panitumumab in the treatment of EGFR-expressing, metastatic colorectal carcinoma comprising administering to a subject in need thereof panitumumab in combination with the ADCC enhancer molecule of the present invention.

In some embodiments, panitumumab is administered in combination with the ADCC enhancer molecule of the present invention for the treatment metastatic colorectal carcinoma. In some embodiments, panitumumab is administered in combination with the ADCC enhancer molecule of the present invention for the treatment metastatic colorectal carcinoma with disease progression on or following fluoropyrimidine, oxaliplatin, and irinotecan chemotherapy regimens.

The dose for panitumumab is preferably between 1-10 mg/kg. This includes 1 mg/kg, 2 mg/kg, 3 mg/kg, 4 mg/kg, 5 mg/kg, 6 mg/kg, 7 mg/kg, 8 mg/kg, 10 mg/kg and points in-between. Preferably, panitumumab is administered by intravenous infusion (e.g., as a 30 min., 45 min., 60 min., 90 min, or 120 min infusion). For example, the dose of panitumumab may be 4 mg/kg administered as a 30-, 60-, or 90-minute intravenous infusion. Doses higher than 1000 mg should be administered over 90 minutes. The frequency of administration may be one time every 7 to 21 days (e.g., once every 10, 14, 18, etc days). The frequency of administration is preferably one time every 14 days Panitumumab may be administered with a higher initial dose followed by lower subsequent doses or maintenance dose. For example, following an initial dose of panitumumab at 6 mg/kg administered as a 90-minute intravenous infusion, subsequent weekly doses may be at 2-4 mg/kg infused over 30 minutes until disease progression or unacceptable toxicity.

Combination with Therapeutic Antibodies and Chemotherapeutic Agents

In certain embodiments, the ADCC enhancer molecule of the invention is administered in combination with one or more therapeutic antibodies and one or more chemotherapeutic agents. A "chemotherapeutic agent" is a chemical compound useful in the treatment of cancer, regardless of mechanism of action. Chemotherapeutic agents include, but are not limited to, the following groups of compounds: cytotoxic antibiotics, antimetabolites, anti-mitotic agents, alkylating agents, platinum containing compounds, arsenic compounds, DNA topoisomerase inhibitors, taxanes, nucleoside analogues, plant alkaloids, and toxins, and synthetic derivatives thereof. The following are non-limiting examples of particular compounds within these groups. Alkylating agents include nitrogen mustards such as cyclophosphamide, ifosfamide, trofosfamide, and chlorambucil; nitrosoureas such as carmustine (BCNU) and lomustine (CCNU); alkylsulphonates such as busulfan and treosulfan; and triazenes such as dacarbazine. Platinum containing compounds include cisplatin, carboplatin, aroplatin, and oxaliplatin. Plant alkaloids include vinca alkaloids such as vincristine, vinblastine, vindesine, and vinorelbine; and taxoids such as paclitaxel and docetaxol. DNA topoisomerase inhibitors include epipodophyllins such as etoposide, teniposide, topotecan, 9-aminocamptothecin, camptothecin, and crisnatol; and mitomycins such as mitomycin C. Anti-folates include DHFR inhibitors such as methotrexate and trimetrexate; IMP dehydrogenase inhibitors such as mycophenolic acid, tiazofurin, ribavirin, hydroxyurea and EICAR; and ribonucleotide reductase inhibitors such as deferoxamine. Pyrimidine analogs include uracil analogs such as 5-fluorouracil, floxuridine, doxifluridine, and ratitrexed; and cytosine analogs such as cytarabine (ara C), cytosine arabinoside, and fludarabine. Purine analogs include mercaptopurine and thioguanine. DNA antimetabolites include 3-HP, 2'-deoxy-5-fluorouridine, 5-HP, alpha-TGDR, aphidicolin glycinate, ara-C, 5-aza-2'-deoxycytidine, beta-TGDR, cyclocytidine, guanazole, inosine glycodialdehyde, macebecin II, and pyrazoloimidazole. Antimitotic agents include allocolchicine, halichondrin B, colchicine, colchicine derivative, dolstatin 10, maytansine, rhizoxin, thiocolchicine, and trityl cysteine.

Other examples of chemotherapeutic agents for use with the ADCC enhancer molecule of the invention include isoprenylation inhibitors; dopaminergic neurotoxins such as 1-methyl-4-phenylpyridinium ion; cell cycle inhibitors such as staurosporine; actinomycins such as actinomycin D and dactinomycin; bleomycins such as bleomycin A2, bleomycin B2, and peplomycin; anthracyclines such as daunorubicin, doxorubicin (adriamycin), idarubicin, epirubicin, pirarubicin, zorubicin, and mitoxantrone; MDR inhibitors such as verapamil; and $Ca^{2+}$ATPase inhibitors such as thapsigargin.

In one embodiment, the ADCC enhancer molecule is administered in combination with one or more of the following: IFNα, IL-2, Dacarbazine (Bayer), Temozolomide (Schering), Tamoxifen (AZ), Carmustine (BMS), Melphalan (GSK), Procarbazine (Sigma-Tau), Vinblastine, carboplatin, cisplatin, taxol, cyclophosphamide, doxorubin, Rituxan (Genentech/Roche), Herceptin (Genentech/Roche), Gleevec, Iressa (AZ), Avastin (Genentech/Roche), Erbitux (ImClone/Merck KGaA), or Tarceva (Genentech/Roche).

In another embodiment, the ADCC enhancer molecule of the invention is administered in combination with one or more of the following: an enediyne such as calicheamicin and esperamicin; duocarmycin, methotrexate, doxorubicin, melphalan, chlorambucil, Ara-C, vindesine, mitomycin C, cis-platinum, etoposide, bleomycin, and 5-fluorouracil.

Suitable toxins and chemotherapeutic agents that can be used in combination with the ADCC enhancer molecule of this invention are described in Remington's Pharmaceutical Sciences, 19th Ed. (Mack Publishing Co. 1995), and in Goodman and Gilman's the Pharmacological Basis of Therapeutics, 7th Ed. (MacMillan Publishing Co. 1985). Other suitable toxins and/or chemotherapeutic agents are known to those of skill in the art.

In certain embodiments, the ADCC enhancer molecule is administered prior to, concurrently with, or subsequent to the administration of the one or more chemotherapeutic agents. In one embodiment, the ADCC enhancer molecule is formulated with one or more chemotherapeutic agents. In another embodiment, the one or more chemotherapeutic agents is administered in a separate pharmaceutical composition. In accordance with this embodiment, the one or more chemotherapeutic agents may be administered to a subject by the same or different routes of administration as those used to administer ADCC enhancer molecule.

ERBITUX® (Cetuximab)

Head and Neck Cancer

In some embodiment the ADCC enhancer molecule of the present invention is used prior to, concurrently with, or subsequent to the administration of one or more chemotherapeutic agents and a therapeutic antibody. The therapeutic antibody is an anti-EGFR (epidermal growth factor receptor) monoclonal antibody. In some embodiment the therapeutic antibody is a human or humanized anti-EGFR monoclonal antibody. In some embodiment the therapeutic antibody is a chimeric anti-EGFR monoclonal antibody. Preferably, the monoclonal antibody is ERBITUX® (cetuximab), a chimeric (mouse/human) monoclonal antibody and epidermal growth factor receptor (EGFR) inhibitor.

Cetuximab may be used in combination with the ADCC enhancer of the present invention and one or more chemotherapeutic agents for the treatment of head and neck cancer. In some embodiments, the ADCC enhancer molecule is used prior to, concurrently with, or subsequent to the administration of one or more chemotherapeutic agents and cetuximab for the treatment of locally or regionally advanced squamous cell carcinoma of the head and neck. In some embodiments, the ADCC enhancer molecule is used prior to, concurrently with, or subsequent to the administration of one or more chemotherapeutic agents and cetuximab for the treatment of recurrent or metastatic squamous cell carcinoma of the head and neck progressing after platinum-based therapy.

According to some embodiments, the invention provides methods of increasing the effectiveness of cetuximab in the treatment of head and neck cancer. Thus, some embodiments provide a method of increasing the clinical effectiveness of cetuximab comprising administering to a subject in need thereof cetuximab in combination with one or more chemotherapeutic agents and the ADCC enhancer molecule of the present invention.

Colorectal Cancer

Cetuximab may be used in combination with the ADCC enhancer of the present invention and one or more chemotherapeutic agents for the treatment of metastatic colorectal cancer. Colorectal cancer includes the well-accepted medical definition that defines colorectal cancer as a medical condition characterized by cancer of cells of the intestinal tract below the small intestine (i.e. the large intestine (colon), including the cecum, ascending colon, transverse colon, descending colon, and sigmoid colon, and rectum). In some embodiments, the ADCC enhancer molecule is used prior to, concurrently with, or subsequent to the administration of cetuximab and one or more chemotherapeutic agents for the treatment of EGFR-expressing metastatic colorectal carcinoma. In some embodiments, the ADCC enhancer molecule is used prior to, concurrently with, or subsequent to the administration of cetuximab and one or more chemotherapeutic agents for the treatment of EGFR-expressing metastatic colorectal carcinoma in patients who are refractory to irinotecan-based chemotherapy.

The invention also provides methods of increasing the effectiveness of cetuximab in the treatment of metastatic colorectal cancer. Thus, some embodiments provide a method of increasing the clinical effectiveness of cetuximab comprising administering to a subject in need thereof cetuximab in combination with one or more chemotherapeutic agents and the ADCC enhancer molecule of the present invention.

HERCEPTIN® (Trastuzumab)

Trastuzumab may be used with the ADCC enhancer of the present invention and one or more chemotherapeutic agents. In some embodiment the ADCC enhancer molecule of the present invention is used prior to, concurrently with, or subsequent to the administration of one or more chemotherapeutic agents and a therapeutic antibody. The therapeutic antibody is an anti-ErbB2 (HER2/neu) monoclonal antibody. In some embodiment the therapeutic antibody is a human or humanized anti-ErbB2 monoclonal antibody. In some embodiment the therapeutic antibody is a chimeric anti-ErbB2 monoclonal antibody.

In some embodiments, the therapeutic antibody is HERCEPTIN® (trastuzumab), a humanized monoclonal antibody that interferes with the human epidermal growth factor receptor 2 (HER2/neu receptor). HER2/neu receptor is a member of the ErbB protein family, more commonly known as the epidermal growth factor receptor family. Trastuzumab reverses the effects of an overactive HER2 receptor.

In some embodiments, trastuzumab is administered in combination with the ADCC enhancer molecule of the present invention and one or more chemotherapeutic agents for the treatment of breast cancer. In some embodiments, the ADCC enhancer molecule is used prior to, concurrently with, or subsequent to the administration of cetuximab and one or more chemotherapeutic agents for the treatment of patients with metastatic breast cancer whose tumors overexpress the HER2 protein.

According to some embodiments, the invention provides methods of increasing the effectiveness of trastuzumab in the treatment of breast cancer. Thus, some embodiments provide a method of increasing the clinical effectiveness of trastuzumab comprising administering to a subject in need thereof trastuzumab in combination with the ADCC enhancer molecule of the present invention and one or more chemotherapeutic agents.

Solid Tumors

According to some embodiments, methods are provided for controlling solid tumor growth (e.g., breast, prostate, melanoma, renal, colon, cervical tumor growth) and/or metastasis comprising administering an effective amount of a compound of the invention to a subject in need thereof. In some embodiments, the subject is a mammal. In some embodiments, the mammal is human.

The term "tumor" is used to denote neoplastic growth which may be benign (e.g., a tumor which does not form metastases and destroy adjacent normal tissue) or malignant/cancer (e.g., a tumor that invades surrounding tissues, and is usually capable of producing metastases, may recur after attempted removal, and is likely to cause death of the host unless adequately treated). As used herein, the terms "tumor", "tumor growth" or "tumor tissue" can be used interchangeably, and refer to an abnormal growth of tissue resulting from uncontrolled progressive multiplication of cells and serving no physiological function.

Hematological Cancers

Hematological cancers are the type of cancer that affects blood, bone marrow, or lymph nodes. As the three are intimately connected through the immune system, a disease affecting one of the three will often affect the others as well. Hematological cancers may derive from either of the two major blood cell lineages: myeloid and lymphoid cell lines. The myeloid cell line normally produces granulocytes, erythrocytes, thrombocytes, macrophages and mast cells; the lymphoid cell line produces B, T, NK and plasma cells. Lymphomas, lymphocytic leukemias, and myeloma are from the lymphoid line, while acute and chronic myelogenous leukemia, myelodysplastic syndromes and myeloproliferative diseases are myeloid in origin.

Hematological cancers which may be treated or ameliorated using compositions of the present invention include, but are not limited to, non-Hodgkin's lymphoma (e.g., small lymphocytic lymphoma, follicular center cell lymphoma, lymphoplasmacytoid lymphoma, marginal zone lymphoma, mantle cell lymphoma, immunoblastic lymphoma, burkitt's lymphoma, lymphoblastic lymphoma, peripheral T-cell lymphoma, anaplastic large cell lymphoma and intestinal T-cell lymphoma), leukemia, acute lymphocytic leukemia, chronic lymphocytic leukemia and plasma cell neoplasms including multiple myeloma.

The present invention provides methods of treating or ameliorating hematological cancers comprising administering an effective amount of a compound of the invention to a subject in need thereof.

KRAS Mutant Cancers

KRAS proto-oncogene encodes K-ras G-protein. This proto-oncogene is a Kirsten ras oncogene homolog from the mammalian ras gene family. A single amino acid substitution, and in particular a single nucleotide substitution, is responsible for an activating mutation. The mutant KRAS protein is implicated in various malignancies, including lung adenocarcinoma, mucinous adenoma, ductal carcinoma of the pancreas and colorectal carcinoma. Several germline KRAS mutations have been found to be associated with Noonan syndrome and cardio-facio-cutaneous syndrome. Somatic KRAS mutations are found at high rates in Leukemias, colon cancer, pancreatic cancer and lung cancer. Patients with KRAS mutation are predictive of a very poor response to some therapeutic antibodies in the treatment of cancers, such as, colorectal cancer and lung cancer.

The invention also provides methods for increasing the clinical effectiveness of a therapeutic monoclonal antibody in treatment of KRAS mutant cancer comprising administering to a subject in need thereof the therapeutic monoclonal antibody, in combination with the ADCC enhancer molecule of the present invention. The therapeutic antibody is for example, panitumumab or cetuximab. A subject in need thereof includes cancer subjects that have been identified as having a KRAS mutation or previously identified as being unresponsive to therapeutic antibody treatment. Subjects having KRAS mutation are identified by methods know in the art such as Pyrosequencing, i.e. nucleotide extension sequencing, genotyping, the ribonuclease, denaturing gradient-gel electrophoresis, carbodiimide, chemical cleavage, single-strand conformation polymorphism, heteroduplex and sequencing methods (Ogino et al. Journal of Molecular Diagnostics, 7: 413-421, 2005).

KRAS Mutant Colorectal Cancer

KRAS proto-oncogene encodes K-ras G-protein, which plays a critical key role in the Ras/mitogen-activated protein kinase (MAPK) signaling pathway located downstream of many growth factor receptors including EGFR and which is involved in colorectal cancer (CRC) carcinogenesis. K-ras recruitment by the activated EGFR is responsible for the activation of a cascade of serine-threonine kinases from the cell surface to the nucleus. KRAS mutations (in exon 2, codons 12 and 13) are present in more than one third of CRC patients and lead to the activation of one of the most important pathways for cell proliferation, the Ras/MAPK pathway, by inducing cyclin D1 synthesis. Consequently, in the presence of a KRAS mutation this pathway activation cannot be significantly inhibited by an anti-EGFR moAb (cetuximab or panitumumab) which acts upstream of the K-ras protein. KRAS mutation is also implicated in other malignancies, including lung adenocarcinoma, mucinous adenoma, and ductal carcinoma of the pancreas.

KRAS Mutant Lung Cancer

Lung cancer remains the leading cause of cancer death in the United States and is expected to cause 162,000 deaths in the United States in 2006. Epidermal growth factor receptor (EGFR), a receptor tyrosine kinase, is expressed in the majority of non-small-cell lung cancers (NSCLC). KRAS mutation, which occurs in 20% to 30% of NSCLCs, mainly in adenocarcinomas (30%) and smokers, has been reported to be associated with poor response to the EGFR-specific tyrosine kinase inhibitors. Patients with KRAS-mutant NSCLC showed poorer clinical outcomes when treated with erlotinib (Tarceva, OSI-774; OSI Pharmaceuticals), small-molecule inhibitors that target the tyrosine kinase domain of the EGFR, and chemotherapy.

FcγR Gene Polymorphisms

The invention also provides methods for increasing the clinical effectiveness of a therapeutic monoclonal antibody in subjects with impaired ADCC function, such as subjects with subjects with FcγR polymorphisms by administering to a subject in need thereof the therapeutic monoclonal antibody, in combination with the ADCC enhancer molecule of the present invention. A subject in need thereof includes subjects that have been identified as having a FcγR polymorphism such as FcγR3a-V158F and FcγR2a-H131R, or previously identified as being unresponsive to therapeutic antibody treatment. Subjects having a FcγR polymorphisms are identified by methods know in the art such as dynamic allele-specific hybridization (DASH), microplate array diagonal gel electrophoresis (MADGE), pyrosequencing, oligonucleotide-specific ligation, the TaqMan system as well as various DNA "chip" technologies such as the Affymetrix SNP chips. These methods require amplification of the target genetic region, typically by PCR. Still other newly developed methods, based on the generation of small signal molecules by invasive cleavage followed by mass spectrometry or immobilized padlock probes and rolling-circle amplification, might eventually eliminate the need for PCR.

FcγR3a-V158F rs396991 is a SNP in the Fc fragment of IgG, low affinity IIIa, receptor (CD16a) FcγR3a gene. rs396991(T) encodes the phenylalanine (F) allele, with the (G) allele encoding the variant valine (V). In this invention, methods are provided for selecting an appropriate therapeutic regimen for a subject in need thereof comprising determining a SNP of FcγR3a at amino acid position 158, wherein a homozygous valine at amino acid position 158 of FcγR3a indicates the subject is predicted to be more responsive to the therapeutic regimen than a subject without the homozygous valine at amino acid position 158 of FcγR3a.

FcγR2a-H131R rs1801274 is a SNP in the Fc fragment of IgG IIa receptor (CD32) FcγR2a gene. The SNP (rs1801274) 131G>A (or H131R) in position 131 of exon 4 of FcγRIIa gene which leads to the substitution of an arginine with a histidine. In this invention, methods are provided for selecting an appropriate therapeutic regimen for a subject in need thereof comprising determining a SNP of FcγR2a at amino acid position 131, wherein a homozygous histidine at amino acid position 131 of FcγR2a indicates the subject is predicted to be more responsive to the therapeutic regimen than a subject without the homozygous histidine at amino acid position 131 of FcγR2a.

Administration of the ADCC Enhancer Molecule

The ADCC enhancer molecule of the invention is preferably formulated for injection, most preferably by subcutaneous injection. In certain embodiments, the ADCC enhancer molecule of the invention is formulated for administration by an intradermal, a transdermal, a subcutaneous, or an intramuscular route. In one embodiment, the ADCC enhancer molecule is formulated for intravenous administration. However, the ADCC enhancer molecule may be formulated for any suitable route of administration, including, by way of example, nasal (e.g., via an aerosol), buccal (e.g., sub-lingual), topical (i.e., administration by either skin and/or mucosal surfaces, including airway surfaces), intrathecal, intra-articular, intraplural, intracerebral, intra-arterial, intraperitoneal, oral, intralymphatic, intranasal, rectal or vaginal administration, by perfusion through a regional catheter, or by direct intralesional injection.

The formulations of the present invention contain an amount of an ADCC enhancer molecule that is effective for the intended use. Particular dosages are also selected based on a number of other factors including the age, sex, species and/or condition of the patient. Effective amounts can also be extrapolated from dose-response curves derived from in vitro test systems or from animal models.

In certain embodiments, the dose of the ADCC enhancer molecule is measured in units of mg/kg of body weight. In other embodiments, the dose is measured in units of mg/kg of lean body weight (i.e., body weight minus body fat content). In other embodiments, the dose is measured in units of mg/m$^2$ of body surface area. In other embodiments, the dose is measured in units of mg per dose administered to a patient. Any measurement of dose can be used in conjunction with the compositions and methods of the invention and dosage units can be converted by means standard in the art.

In some embodiments, the dose for the ADCC enhancer molecule is between 0.1-10 mg/m$^2$ (e.g., 0.1-3.9 mg/m2, 0.1-1 mg/m$^2$, 0.1-2 mg/m$^2$, 0.1-4 mg/m$^2$, 2-4 mg/m$^2$, 2-6 mg/m$^2$, 2-8 mg/m$^2$). This includes 0.003 mg/m$^2$, 0.1 mg/m$^2$, 1 mg/m$^2$, 2 mg/m$^2$, 3 mg/m$^2$, 4 mg/m$^2$, 5 mg/m$^2$, 6 mg/m$^2$, 7 mg/m$^2$, 8 mg/m$^2$ and points in-between. The frequency of administration is preferably once every 7 to 21 days (e.g., once every 7, 10, 14, 18, 21 days). In some embodiments, the frequency of administration is preferably 1, 2, or 3 times every 7 to 21 days (e.g., once every 7, 10, 14, 18, 21 days). The ADCC enhancer molecule may be given until disease progression or unacceptable toxicity. In some embodiments, 2-20 doses are given (e.g., 2, 4, 6, 8, 10, 12, 14, 16, 18, 20 doses). The preferred route of administration is subcutaneous.

Examples of dosing regimens that can be used in the methods of the invention include, but are not limited to, daily, three times weekly (intermittent), weekly, or every 14 days. In certain embodiments, dosing regimens include, but are not limited to, monthly dosing or dosing every 6-8 weeks. In a preferred embodiment, an ADCC enhancer molecule formulation of the present invention is administered by subcutaneous injection weekly or biweekly in combination with a suitable treatment modality for the treatment of cancer or infectious disease in a subject, preferably a human subject.

Exemplary doses of an ADCC enhancer molecule include milligram amounts per kilogram of the subject. In one embodiment, the dose is from about 0.02 to 10 mg/kg of body weight or about 0.04 to 5 mg/kg of body weight. In a specific embodiment, the dosage is about 0.05 mg/kg, about 0.1 mg/kg, about 0.5 mg/kg, about 1 mg/kg, about 5 mg/kg, or about 10 mg/kg of the subject's body weight.

In certain embodiments of the methods for treating cancer or infectious disease, the ADCC enhancer molecule is administered to the subject at a dose of from about 0.02 to 10 mg/kg of body weight or about 0.04 to 5 mg/kg of body weight of the subject. In particular embodiments, the ADCC enhancer molecule is administered at a dose of about 0.05 mg/kg, about 0.1 mg/kg, about 0.5 mg/kg, about 1 mg/kg, about 5 mg/kg, or about 10 mg/kg of the subject's body weight. In certain further embodiments, the ADCC enhancer molecule formulation is administered to the subject on a weekly or biweekly basis. In specific embodiments, a daily dose is at least 0.05 mg, 0.50 mg, 1.0 mg, 5.0 mg, 10 mg, 15 mg, 20 mg, 30 mg, or at least 50 mg.

Recommended dosages for intradermal, intramuscular, intraperitoneal, subcutaneous, epidural, or intravenous administration are in the range of about 0.02 to 10 mg/kg of body weight per day. Suitable doses for topical administration are in the range of about 0.001 milligram to about 50 milligrams per kilogram of body weight per day, depending on the area of administration. Those skilled in the art will appreciate that dosages are generally higher and/or frequency of administration greater for initial treatment as compared with maintenance regimens.

Kits

The present invention provides a pharmaceutical pack or kit comprising one or more containers filled with a liquid or lyophilized ADCC enhancer molecule. In preferred embodiments the liquid or lyophilized formulation is sterile. In one embodiment, the kit comprises a liquid or lyophilized formulation of the ADCC enhancer molecule, in one or more containers, and one or more other prophylactic or therapeutic agents useful for the treatment of cancer or B-cell disorders. The one or more other prophylactic or therapeutic agents may be in the same container as the ADCC enhancer molecule or in one or more other containers. Preferably, the ADCC enhancer molecule is formulated at a concentration of from about 0.5 mg/ml to about 50 mg/ml, from about 1 mg/ml to about 40 mg/ml, or from about 2 mg/ml to about 15 mg/ml, and the formulation is suitable for administration by an intradermal, a transdermal, a subcutaneous, or an intramuscular route. Alternatively, the ADCC enhancer molecule is formulated for intravenous administration. The ADCC enhancer molecule may also be formulated for any suitable route of administration, including, by way of example, nasal (e.g., via an aerosol), buccal (e.g., sublingual), topical (i.e., administration by either skin and/or mucosal surfaces, including airway surfaces), intrathecal, intra-articular, intraplural, intracerebral, intra-arterial, intraperitoneal, oral, intralymphatic, intranasal, rectal or vaginal administration, by perfusion through a regional catheter, or by direct intralesional injection. Preferably, the kit contains the ADCC enhancer molecule in unit dosage form. Most preferably, the unit dosage form is in a form suitable to provide a unit dose of about 0.02 to 10 mg/kg or about 0.04 to 5 mg/kg of body weight of the subject to be treated.

In certain embodiments, the kit further comprises one or more therapeutic monoclonal antibodies, for example, but are not limited to, rituximab, cetuximab, panitumumab, trastuzumab, alemtuzumab, epratuzumab, basiliximab, daclizmab, labetuzumab, seviumab, tuvurimab, palivizumab, infliximab, omalizumab, efalizuab, natalizumab, and clenoliximab. The kit may also comprise one or more chemotherapeutic agents. The kit of the present invention further comprises instructions for use in the treatment of cancer (e.g., using the liquid formulations of the invention alone or in combination with another prophylactic or therapeutic agent), as well as side effects and dosage information for one or more routes of administration. Optionally associated with such container(s) is a notice in the form prescribed by a governmental agency regulating the manufacture, use or sale of pharmaceuticals or biological products, which notice reflects approval by the agency of manufacture, use or sale for human administration.

Compositions

Also include in the invention are composition containing an ADCC enhancer molecule and a therapeutic antibody. The therapeutic antibody is for example, but not limited to, rituximab, cetuximab, panitumumab, trastuzumab, alemtuzumab, epratuzumab, basiliximab, daclizmab, labetuzumab, seviumab, tuvurimab, palivizumab, infliximab, omalizumab, efalizuab, natalizumab, or cleneliximab.

Definitions

Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, suitable methods and materials are described below. All publications, patent applications, patents, and other references mentioned herein are incorporated by reference in their entirety. In the case of conflict, the present specification, including definitions, will control. In addition, the materials, methods, and examples are illustrative only not intended to be limiting. Other features and advantages of the invention will be apparent from the following detailed description and claims.

The term "administration", "administering", "co-administration", or co-administering" refers to both concurrent and sequential administration of the active agents.

A "subject" or "patient" in the context of the present invention is preferably a mammal. The mammal can be a human, non-human primate, mouse, rat, dog, cat, horse, or cow, but are not limited to these examples. A subject can be male or female.

"ADCC activity" as used herein refers to an activity to damage a target cell (e.g., tumor cell) by activating an effector cell via the binding of the Fc region of an antibody to an Fc receptor existing on the surface of an effector cell such as a killer cell, a natural killer cell, an activated macrophage or the like. An activity of antibodies of the present invention includes ADCC activity. ADCC activity measurements and antitumor experiments can be carried out in accordance using any assay known in the art.

The term "enhances antibody-dependent cellular cytotoxicity", "enhances ADCC" (e.g. referring to cells), or "increasing ADCC" is intended to include any measurable increase in cell lysis when contacted with a therapeutic antibody and the ADCC enhancer molecule as compared to the cell killing of the same cell in contact with therapeutic antibody alone. For example, an increase in cell lysis may be by at least about 10%, 20%, 30%, 40%, 50%, 60%, 70%, 80%, 90%, 100%, 150%, 200%, 250%, 300%, 325%, 400%, or 500%.

The term "monoclonal antibody" or "monoclonal antibody composition" as used herein refer to a preparation of antibody molecules of single molecular composition. A monoclonal antibody composition displays a single binding specificity and affinity for a particular epitope.

The term "human antibody", as used herein, is intended to refer to antibodies having variable regions in which both the framework and CDR regions are derived from human germline immunoglobulin sequences. Furthermore, if the antibody contains a constant region, the constant region also is derived from human germline immunoglobulin sequences. The human antibodies of the invention may include amino acid residues not encoded by human germline immunoglobulin sequences (e.g., mutations introduced by random or site-specific mutagenesis in vitro or by somatic mutation in vivo).

The term "human monoclonal antibody" refers to antibodies displaying a single binding specificity which have variable regions in which both the framework and CDR regions are derived from human germline immunoglobulin sequences. In one embodiment, the human monoclonal antibodies are produced by a hybridoma which includes a B cell obtained from a transgenic nonhuman animal, e.g., a transgenic mouse, having a genome comprising a human heavy chain transgene and a light chain transgene fused to an immortalized cell. The term "human monoclonal antibody", as used herein, also includes all human antibodies that are prepared, expressed, created or isolated by recombinant means, such as (a) antibodies isolated from an animal (e.g., a mouse) that is transgenic or transchromosomal for human immunoglobulin genes or a hybridoma prepared therefrom (described further below), (b) antibodies isolated from a host cell transformed to express the human antibody, e.g., from a transfectoma, (c) antibodies isolated from a recombinant, combinatorial human antibody library, and (d) antibodies prepared, expressed, created or isolated by any other means that involve splicing of human immunoglobulin gene sequences to other DNA sequences. Such recombinant human antibodies have variable regions in which the framework and CDR regions are derived from human germline immunoglobulin sequences. In certain embodiments, however, such recombinant human antibodies can be subjected to in vitro mutagenesis (or, when an animal transgenic for human Ig sequences is used, in vivo somatic mutagenesis) and thus the amino acid sequences of the $V_H$ and $V_L$ regions of the recombinant antibodies are sequences that, while derived from and related to human germline $V_H$ and $V_L$ sequences, may not naturally exist within the human antibody germline repertoire in vivo.

The term "humanized antibody" is intended to refer to antibodies in which CDR sequences derived from the germline of another mammalian species, such as mouse, have been grafted onto human framework sequences. Additional framework region modifications may be made within the human framework sequences.

The term "chimeric antibody" is intended to refer to antibodies in which the variable region sequences are derived from one species and the constant region sequences are derived from another species, such as an antibody in which the variable region sequences are derived from a mouse antibody and the constant region sequences are derived from a human antibody.

A "mutated gene" or "mutation" or "functional mutation" or "mutant" refers to an allelic form of a gene, which is capable of altering the phenotype of a subject having the mutated gene relative to a subject which does not have the mutated gene. The altered phenotype caused by a mutation can be corrected or compensated for by certain agents. If a subject must be homozygous for this mutation to have an altered phenotype, the mutation is said to be recessive. If one copy of the mutated gene is sufficient to alter the phenotype of the subject, the mutation is said to be dominant. If a subject has one copy of the mutated gene and has a phenotype that is intermediate between that of a homozygous and that of a heterozygous subject (for that gene), the mutation is said to be co-dominant.

The term "polymorphism" refers to the coexistence of more than one form of a gene or portion (e.g., allelic variant) thereof. A portion of a gene of which there are at least two different forms, i.e., two different nucleotide sequences, is referred to as a "polymorphic region of a gene". A specific genetic sequence at a polymorphic region of a gene is an allele. A polymorphic region can be a single nucleotide, the identity of which differs in different alleles. A polymorphic region can also be several nucleotides long.

The term "wild-type allele" refers to an allele of a gene which, when present in two copies in a subject results in a wild-type phenotype. There can be several different wild-type alleles of a specific gene, since certain nucleotide changes in a gene may not affect the phenotype of a subject having two copies of the gene with the nucleotide changes.

As used throughout this disclosure, the singular forms "a," "an," and "the" include plural reference unless the context clearly dictates otherwise. Thus, for example, a reference to "a composition" includes a plurality of such compositions, as well as a single composition, and a reference to "a therapeutic agent" is a reference to one or more therapeutic and/or pharmaceutical agents and equivalents thereof known to those skilled in the art, and so forth. Thus, for example, a reference to "a host cell" includes a plurality of such host cells, and a reference to "an antibody" is a reference to one or more antibodies and equivalents thereof known to those skilled in the art, and so forth. Further, the use of the word "a" or "an" when used in conjunction with the term "comprising" in the claims and/or the specification may mean "one," but it is also consistent with the meaning of "one or more," "at least one," and "one or more than one."

Throughout this application, the term "about" is used to indicate that a value includes the standard deviation of error for the device or method being employed to determine the value.

The use of the term "or" in the claims is used to mean "and/or" unless explicitly indicated to refer to alternatives only or the alternatives are mutually exclusive, although the disclosure supports a definition that refers to only alternatives and "and/or."

As used in this specification and claim(s), the words "comprising" (and any form of comprising, such as "comprise" and "comprises"), "having" (and any form of having, such as "have" and "has"), "including" (and any form of including, such as "includes" and "include") or "containing" (and any form of containing, such as "contains" and "contain") are inclusive or open-ended and do not exclude additional, unrecited elements or method steps.

The term "effective amount" of refers to an amount sufficient to provide the desired anti-cancer effect, anti-tumor effect or anti-disease effect in an animal, preferably a human, suffering from cancer or a cellular disease. Desired anti-tumor effects include, without limitation, the modulation of tumor growth (e.g. tumor growth delay), tumor size, or metastasis, the reduction of toxicity and side effects associated with a particular anti-cancer agent, the amelioration or minimization of the clinical impairment or symptoms of cancer, extending the survival of the subject beyond that which would otherwise be expected in the absence of such treatment, and the prevention of tumor growth in an animal lacking any tumor formation prior to administration, i.e., prophylactic administration.

EXAMPLES

It is understood that modifications which do not substantially affect the activity of the various embodiments of this invention are also provided within the definition of the invention provided herein. Accordingly, the following examples are intended to illustrate but not limit the present invention. While the claimed invention has been described in detail and with reference to specific embodiments thereof, it will be apparent to one of ordinary skill in the art that various changes and modifications can be made to the claimed invention without departing from the spirit and scope thereof. Thus, for example, those skilled in the art will recognize, or be able to ascertain, using no more than routine experimentation, numerous equivalents to the specific substances and procedures described herein. Such equivalents are considered to be within the scope of this invention, and are covered by the following claims.

Example 1. Enhancement of the Therapeutic Effectiveness of Monoclonal Antibody Therapy by Enhancing NK Activity and ADCC Including ADCC in Genetically Resistant Populations A subcutaneous formulation comprising the ADCC enhancer {2-amino-8-[4-(pyrrolidinylcarbonyl)phenyl]-(3H-benzo[f]azepin-4-yl)}-N,N-dipropylcarboxamide was used for the experiments. The structure for {2-amino-8-[4-(pyrrolidinylcarbonyl)phenyl]-(3H-benzo[f]azepin-4-yl)}-N,N-dipropylcarboxamide is as follows:

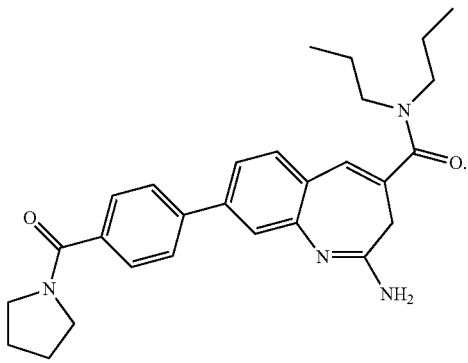 [SMILES: CCCN(CCC)C(=O)C1=Cc2ccc(-c3ccc(C(=O)N4CCCC4)cc3)cc2N=C(N)C1]

Stimulation of PBMCs:

Human Peripheral blood mononuclear cells (PBMCs) were isolated by Ficoll™ density gradient centrifugation and resuspended in RPMI containing 2% heat-inactivated FBS. PBMCs at a concentration of 1 to 3 million cells per mL were incubated with 10-500 nM ADCC enhancer in a humidified $CO_2$ incubator for 18-72 hrs. Activated PBMCs were then used as effector cells in NK and ADCC assays.

NK and ADCC Assays:

PBMCs activated with the ADCC enhancer were tested for the ability to enhance killing of the NK sensitive target cell line K562 or various tumor cells coated with monoclonal antibodies. Target cells were labeled with the fluorescent dye Calcein AM for 1 hour at 37° C. in a dark humidified $CO_2$ incubator. Labeled targets ($2\times10^5$ cells/mL) were then incubated with monoclonal antibodies such as Herceptin, Rituxan, and Erbitux at a concentration of 5 micrograms/mL for 30 minutes at 4 C after which any unbound antibody was washed away. Activated effector cells and labeled target cells were incubated in 96-well tissue culture plates at for 4 hours at 37° C. in a dark humidified $CO_2$ incubator in an assay buffer containing HBSS+Ca/Mg+5% FBS. The ratio of effector to target cells (E:T ratio) was varied for example from 1:3 to 1:100. At the end of the incubation cells were pelleted by centrifugation and 100 microliters of supernatant was transferred to a 96-well flat-bottom black plates (Microfluor 1 Black Flat Bottom Microtiter Plates—Thermo/Fisher #7605). Fluorecence was quantified with a fluorescent microtiter plate reader. The % specific lysis was calculated as (Sample fluorescence-spontaneous fluorescence)*100/ (100% fluorescence-spontaneous). 100% fluorescence was determined from wells that contained labeled target cells and detergent such at 0.1% Tween-20 or Triton X-100. Spontaneous fluorescence was determined from wells that contained assay buffer and target cells but not effector cells.

Results

To determine whether the lytic function of NK cells was augmented by the ADCC enhancer, a series of cytotoxicity studies was conducted. Human peripheral blood mononuclear cells (PBMCs) were stimulated with the ADCC enhancer then tested for the ability lyse the NK sensitive target cells K562. As shown in FIG. 1, the ADCC enhancer enhanced lysis of K562 target cells in a dose dependent fashion. PBMC effector cells that were incubated with buffer control lysed less than 20% of the target cells while PBMCs that had been stimulated with 167 nM ADCC enhancer killed up to 45% of the target cells and PBMC that had been stimulated with 500 nM ADCC enhancer lysed greater than 90% of the target cells.

Figure 2:
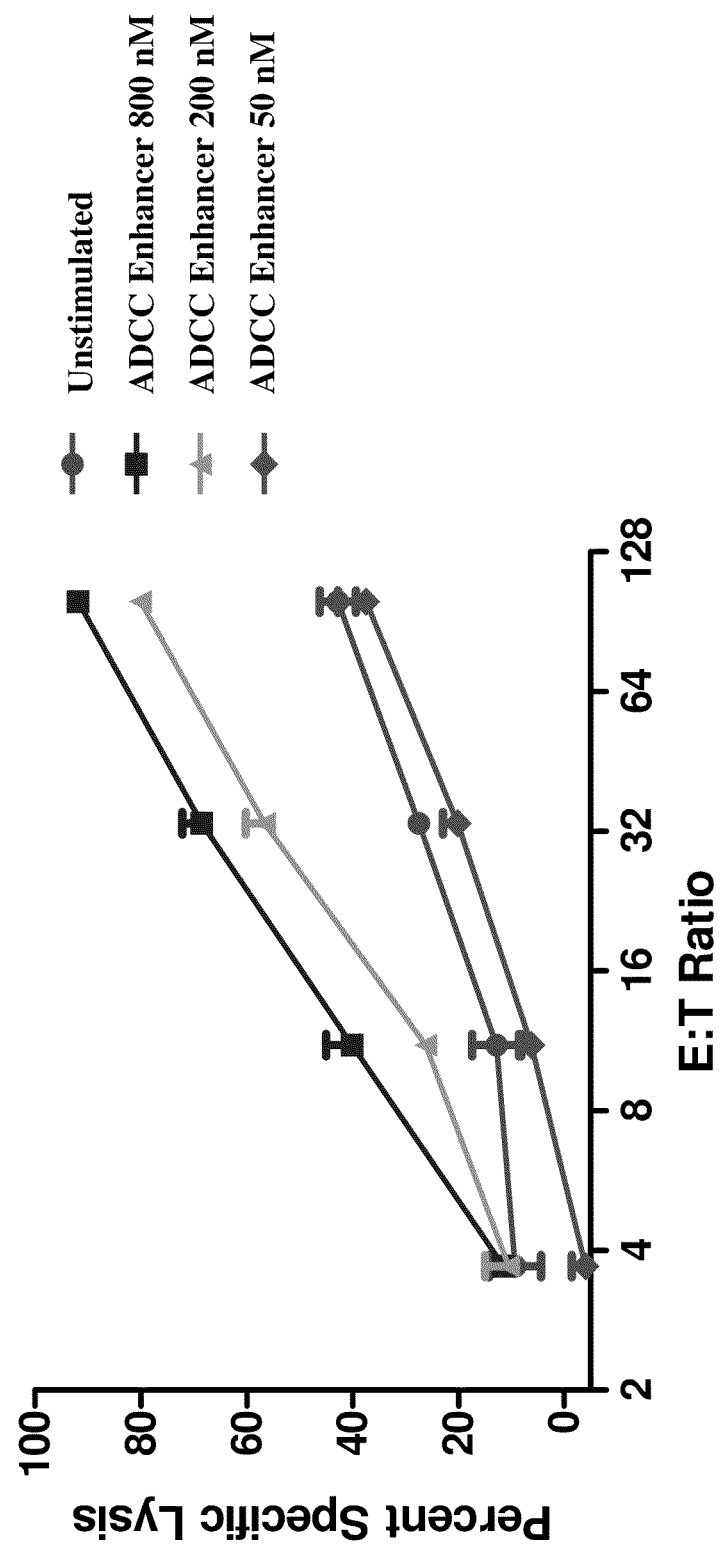
FIG. 2 shows that the ADCC enhancer enhances ADCC with Rituxan. Calcein AM labeled HS-Sultan cells coated with Rituxan were incubated with PBMC effector cells that had been previously stimulated with the ADCC enhancer. Percent specific lysis of target cells was evaluated over a range of effector:target cell ratios.

In addition to direct lysis of NK sensitive targets, PBMCs stimulated with the ADCC enhancer enhanced antibody dependent cellular cytotoxicity. As shown FIG. 2, the ADCC enhancer enhanced Rituxan mediated ADCC of the B cell lymphoma cell line HS-Sultan. When Rituxan coated HS-Sultan cells were incubated with unstimulated PBMCs, cell killing ranged from 9% to approximately 40% over a range of effector: target cell ratios (E:T ratio). In contrast, cell killing was as high as 80 and 90% when the Rituxan coated target cells were incubated with PBMCs that had been activated by the ADCC enhancer. The enhancement of ADCC was dose dependent and increased as the E:T ratio increased.

Figures 3A, 3B, 3C, 3D:
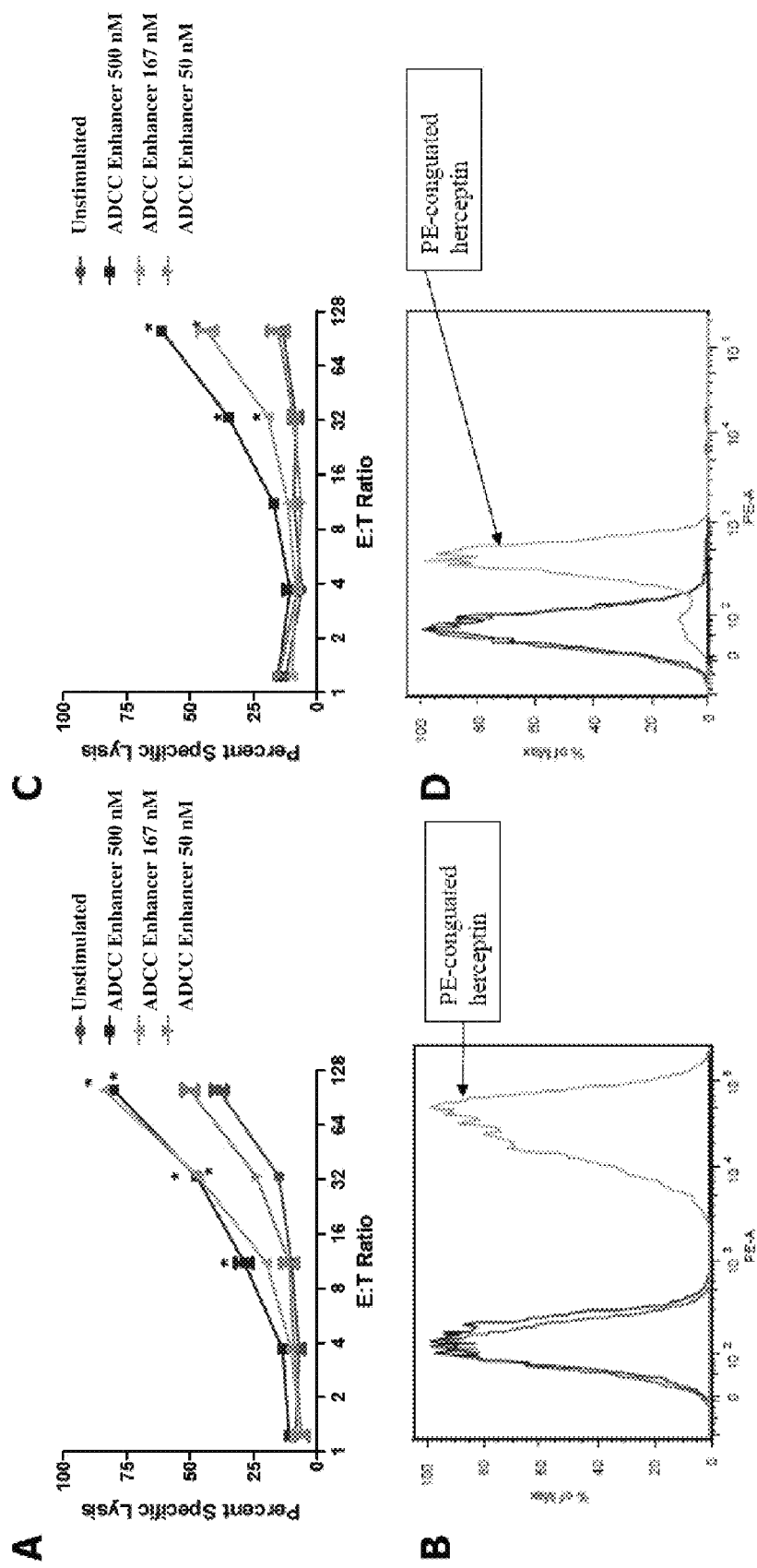
FIG. 3 shows that the ADCC enhancer enhances ADCC with Herceptin in both SKBR3 cell line that expresses high levels of the Her2neu tumor antigen and the MDA-MB-231 cell line that expressed lower levels of the tumor antigen. Calcein AM labeled SKBR3 cells (Panel A) or MDA-MB-231 cells (Panel C) coated with Herceptin were incubated with PBMC effector cells that had been previously stimulated with the ADCC enhancer. Percent specific lysis of target cells was evaluated over a range of effector:target cell ratios. Her2neu expression was quantified by flow cytomerty using PE-conjugated herceptin (green line) or controls (#1 and #2) in SKBR3 (Panel B) and MDA-MB-231 (Panel D) breast cancer cell lines.

For some patients that express only low levels of tumor antigens ADCC is less efficient. As shown in FIG. 3, the ADCC enhancer enhanced lysis of Herceptin coated target cells from both the breast cancer cell line SKBR3 that expresses high levels of the Her2neu tumor antigen and the breast cancer cell line MDA-MB-231 that expresses lower levels of the tumor antigen. When Herceptin coated cells were incubated with unstimulated PBMCs, cell killing was as high as 40% in the SKBR3 cell line but only less that 15% in the MDA-MB-231 cell line. Activation of PBMCs with the ADCC enhancer enhanced Herceptin-mediated ADCC in both cells lines, killing greater that 80% of the SKBR3 targets and approximately 40-60% of the MDA-MB-231 targets. The responses were dependent on the concentration of the ADCC enhancer used to stimulate the effector cells and on the ratio of effector cells to target cells.

Example 2. Polymorphisms of FcγR and Cancer Treatment

ADCC is mediated through immune effector cells included NK cells that engage the Fc portion of the monoclonal antibody through specific receptors. Patients with single nucleotide polymorphisms in these receptors such as FcRgamma3a position 158 and FcRgamma2a position 131 have a poorer clinical prognosis presumably from poor ADCC due to a lower affinity of the receptor for the monoclonal antibody. Previous studies have found that a polymorphism in the FcγR3A molecule (158F/V) that alters the molecule's affinity for IgG1 is an important factor determining the clinical efficacy seen with some monoclonal antibodies (mAbs) used in the treatment of cancer. To determine if this common polymorphism affects the baseline antibody-dependent cellular cytotoxicity (ADCC) response and/or response to the ADCC enhancer molecule of the present invention (Compound VTX-2337), PBMCs from donors were genotyped for the two alleles encoding the F and V isoforms, respectively, and tested in vitro. We analyzed rituximab-mediated ADCC using unstimulated PBMC or VTX-2337-stimulated PBMC from 15 donors, including 10 donors with FF or FV phenotype and 5 donors with VV phenotype.

Blood was collected from healthy donors and PBMCs were isolated using a Ficoll gradient. PBMCs were activated by culturing them in the presence of 500 nM VTX-2337 at 37° C. in a humidified 5% CO2 incubator for 48 hours. Activated PBMCs were then incubated with rituximab-coated HS-Sultan cells loaded at a ratio of 100:1 for 4 hours. Lysis was determined by measuring release of the fluorescent dye Calcein AM from the HS-Sultan cells.

Figure 4:
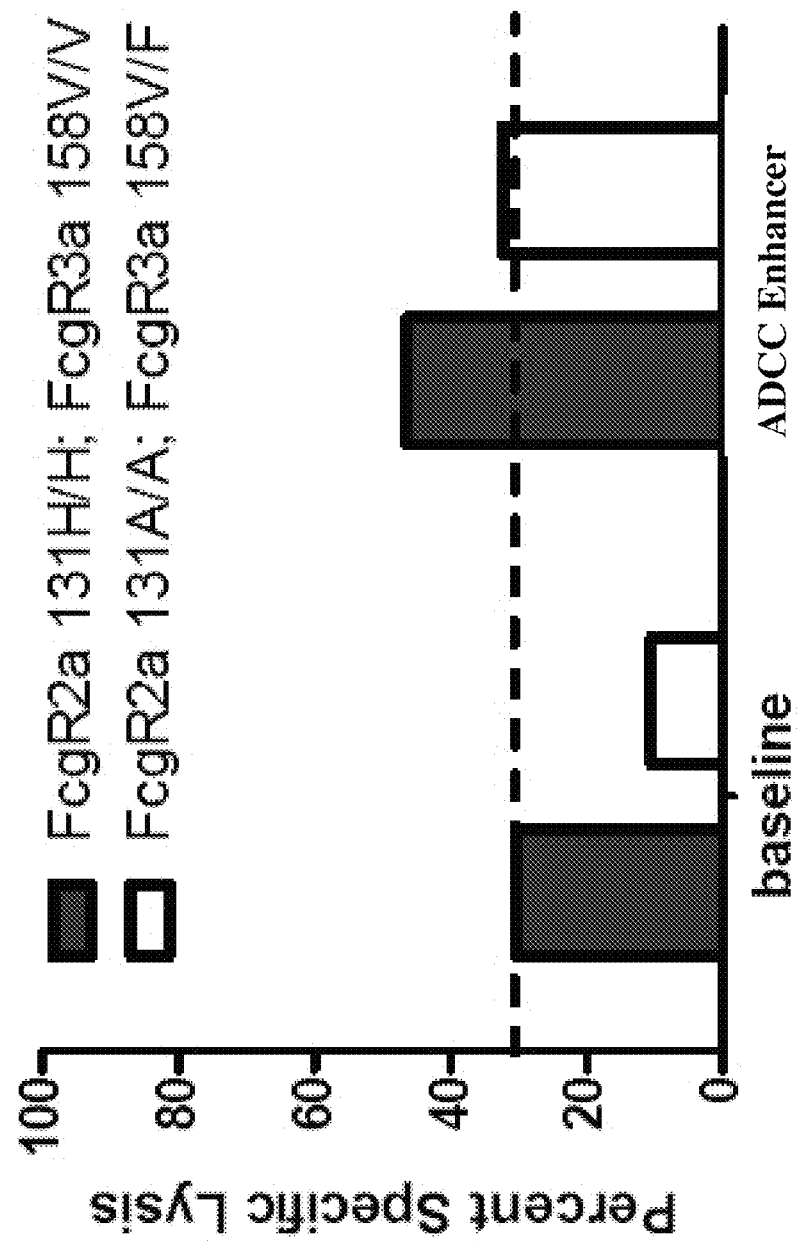
FIG. 4 shows that the ADCC enhancer enhances Rituxan-mediated ADCC in cells from patients with high affinity Fc receptors and low affinity Fc receptors. Percent specific lysis is shown for Rituxan-coated HS-Sultan cells incubated with PBMC effector cells at an E:T ratio of 50:1. PBMCs from a patient with the high affinity genotype FcgR2a131 H/H and FcgR3a V/V (solid rectangles) or a patient with the lower affinity genotype FcgR2a131 A/A and FcgR3a V/F (open rectangles) were evaluated for ADCC after stimulation with buffer control (baseline) or stimulation with 500 nM ADCC enhancer.

As shown in the FIG. 4, baseline ADCC in cells from a patient with a high affinity genotype was approximately 30% while baseline ADCC in cells from a patient with a lower affinity genotype was 10%. Stimulation of PBMCs with the ADCC enhancer enhanced ADCC in both patients. In the patient with the low affinity genotype ADCC increased from 10% to 30%. Thus, the ADCC enhancer "rescued" the poor genotype and increased ADCC to baseline levels of the wild type genotype.

Figure 5:
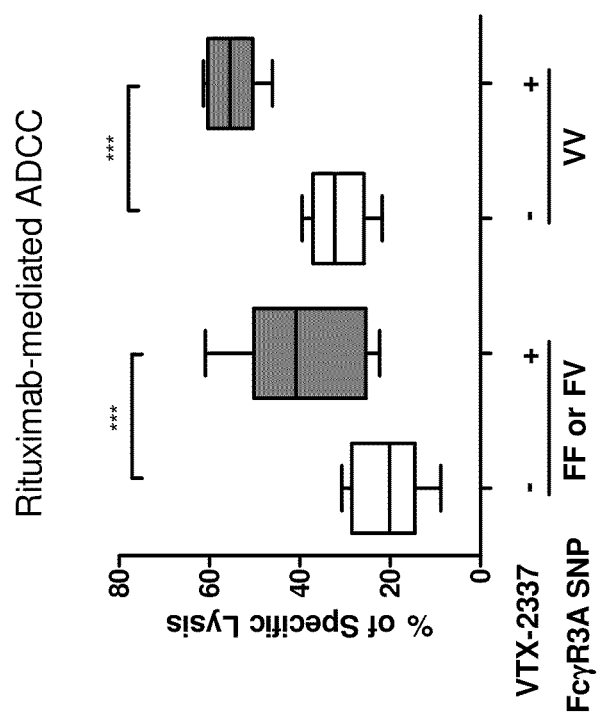
FIG. 5 shows that the patients with FcgR3a FF or FcgR3a FV have significantly reduced rituximab-mediated ADCC activity than individuals with the FcgR3a VV phenotype.

FIG. 5 shows that, the FF or FV donors have significantly reduced rituximab-mediated ADCC activity than individuals with the VV phenotype (20.5±2.5% specific lysis for FF/FV vs. 31.7±2.9% specific lysis for VV, p=0.017). When PBMC were stimulated with VTX-2337 before mixing with target tumor cells, the resulting levels of ADCC were significantly enhanced, in both FF/FV group and VV group. ADCC was enhanced from 20.5±2.5% to 40.0±4.1% in low affinity FF/FV group (p=0.0007) and from 31.7±2.9% to 55.5±2.6 in the high affinity VV group (p=0.0003). There is no significant difference between stimulated PBMC from FF/FV donors and unstimulated PBMC from VV donors, indicating that the presence of VTX-2337 may enhance ADCC from donors with low affinity SNP to a level normally only achieved by PBMC from high affinity donors.

What is claimed is:

1. A method of increasing antibody-dependent cellular cytotoxicity (ADCC) in a subject receiving therapeutic monoclonal antibody treatment comprising administering to the subject a therapeutic monoclonal antibody and an ADCC enhancer molecule in an amount sufficient to increase ADCC, wherein the ADCC enhancer molecule is {2-amino-8-[4-(pyrrolidinylcarbonyl)phenyl]-(3H-benzo[f]azepin-4-yl)}-N,N-dipropylcarboxamide.

2. The method of claim 1, wherein the therapeutic monoclonal antibody is a therapeutic anti-CD20 monoclonal antibody, a therapeutic anti-Her2 monoclonal antibody, or a therapeutic anti-EGFR monoclonal antibody.

3. The method of claim 1, wherein the therapeutic monoclonal antibody is rituximab, trastuzumab, cetuximab, or panitumumab.

4. The method of claim 1, further comprising administering to the subject a therapeutically effective amount of one or more chemotherapeutic agents.

5. The method of claim 1, wherein the subject has an FcγR polymorphism or a KRAS mutation.

6. The method of claim 1, wherein the subject has previously been identified as being unresponsive to therapeutic antibody treatment.

7. The method of claim 1, wherein the subject has impaired ADCC function.

8. The method of claim 1, wherein the ADCC enhancer molecule is administered prior to, concurrently with, subsequent to the administration of the therapeutic antibody.

* * * * *